United States Patent [19]

Sato et al.

[11] 4,228,168
[45] Oct. 14, 1980

[54] AZEPINO [1,2,3-LM]-β-CARBOLINE COMPOUNDS AND PHARMACEUTICAL COMPOSITION THEREOF

[75] Inventors: Yasuhiko Sato, Urawa; Tomishige Mizoguchi, Wako; Yukitsuka Kudo, Osaka; Ryuichi Ishida, Suita, all of Japan

[73] Assignee: Tanabe Seiyaku Co., Ltd., Osaka, Japan

[21] Appl. No.: 90,528

[22] Filed: Nov. 2, 1979

[30] Foreign Application Priority Data

Nov. 22, 1978 [GB] United Kingdom ............... 45665/78

[51] Int. Cl.$^3$ .................. C07D 471/14; A61K 31/55
[52] U.S. Cl. ............................ 424/256; 260/239.3 P
[58] Field of Search ................. 260/239.3 P; 424/256

[56] References Cited

PUBLICATIONS

Laronze et al., "Bull. Soc. Chim. France" (1977), Nos. 11–12, pp. 1207–1214.

*Primary Examiner*—John D. Randolph
*Assistant Examiner*—Robert T. Bond
*Attorney, Agent, or Firm*—Bierman & Bierman

[57] ABSTRACT

An azepino[1,2,3-lm]-β-carboline compound of the formula:

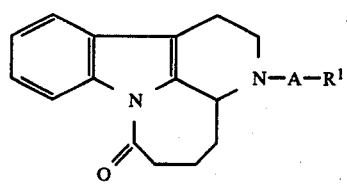

[I]

wherein $R^1$ is hydrogen, cycloalkyl of 3 to 7 carbon atoms, phenyl, hydroxy, alkoxycarbonyl of 2 or 3 carbon atoms or alkanoyl of 2 or 3 carbon atoms, and A is single bond or straight or branched alkylene of one to 5 carbon atoms. Several methods of preparing the compound [I] are disclosed. The compound [I] and a pharmaceutical acceptable acid addition salt thereof have a potent anti-anoxic activity.

7 Claims, No Drawings

AZEPINO [1,2,3-LM]-β-CARBOLINE COMPOUNDS AND PHARMACEUTICAL COMPOSITION THEREOF

This invention relates to a novel azepino[1,2,3-lm]-β-carboline compound and processes for preparing the same. More particularly, it relates to a 1,2,3,3a,4,5,6,7-octahydro-7-oxo-azepino[1,2,3-lm]-β-carboline compound of the formula:

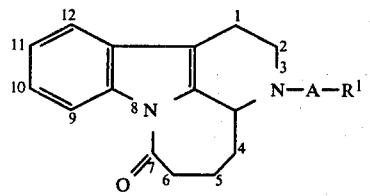

wherein $R^1$ is hydrogen, cycloalkyl of 3 to 7 carbon atoms, phenyl, hydroxy, alkoxycarbonyl of 2 or 3 carbon atoms or alkanoyl of 2 or 3 carbon atoms, and A is single bond or straight or branched alkylene of one to 5 carbon atoms, or a pharmaceutically acceptable acid addition salt thereof.

Bulletin de la Societe Chimique de France 1977(No. 11-12), pages 1207-1214 descloses that 1,2,3,3a,4,5,6,7-octahydro-3-methyl-4-ethyl-7-oxo-azepino[1,2,3-lm]-β-carboline is prepared by intramolecular cyclization of 1,2,3,4-tetrahydro-1-(1-ethyl-3-methoxycarbonyl-propyl)-2-methyl-β-carboline. Said literature also discloses that the above-mentioned 4-ethyl-7-oxo-azepino[1,2,3-lm]-β-carboline is useful as an intermediate in the synthesis of vincamine analogs.

As a result of various investigations, however, we have now found that the compound [I] has a potent anti-anoxic activity and is useful to enhance oxygenation of tissues, especially brain oxygenation. For example, when male mice weighing about 20 g were kept under reduced oxygen tension (4.3% oxygen, atmospheric pressure: 165 mmHg) 15 minutes after intraperitoneal administration of a test compound, $SD_{50}$ (i.e., the dose required to produce 50% increase in the survival time of mice as compared with that of a group of non-medicated mice) of 1,2,3,3a,4,5,6,7-octahydro-3-methyl-7-oxo-azepino[1,2,3-lm]-β-carboline hydrochloride, 1,2,3,3a,4,5,6,7-octahydro-3-cycloheptyl-7-oxo-azepino[1,2,3-lm]-β-carboline hydrochloride and 1,2,3,3a,4,5,6,7-octahydro-3-cyclohexylmethyl-7-oxo-azepino[1,2,3-lm]-β-carboline hydrochloride were 4.7 mg/kg, 7.39 mg/kg and 14.1 mg/kg, respectively.

The azepino[1,2,3-lm]-β-carboline compound [I] of the present invention is useful for treatment or prophylaxis of various hypoxia which may occur due to cerebral apoplexia, craniotrauma or brain ischemia. For example, it may be employed for treatment or prophylaxis of amnesia, disorientation, clouding of consciousness and other consciousness disturbances. The compound [I] of the invention may also be employed for treatment of patients who are undergoing long-lasting surgical procedures involving the liability of transitory cerebral hypoxia. The compound [I] may further be used in alleviating the symptoms of senile demensia.

Further, the compound [I] of the invention may be effective to improve coronary blood flow because of a coronary vasodilating activity thereof. When the effect of each test compounds upon the coronary outflow was measured by the use of guinea pig's isolated heart (Langendorff method), the 3-n-propyl-, 3-cycloheptyl-, 3-(2-acetylethyl)-, 3-(2-hydroxyethyl)- and 3-(2-hydroxy-n-propyl)-derivatives of 1,2,3,3a,4,5,6,7-octahydro-7-oxo-azepino[1,2,3-lm]-β-carboline hydrochloride showed the coronary vasodilating activity at least as strong as that of papaverine.

Concomitantly, the toxicity of the compound [I] is low. For example, when administered intraperitoneally to mice, the 50% lethal dose (estimated from the number of mice died 7 days after the administration) of 1,2,3,3a,4,5,6,7-octahydro-3-cycloheptyl-7-oxo-azepino[1,2,3-lm]-β-carboline hydrochloride and 1,2,3,3a,4,5,6,7-octahydro-3-benzyl-7-oxo-azepino[1,2,3-lm]-β-carboline hydrochloride were about 1300 and about 3800 mg/kg, respectively.

The compound [I] of the present invention can be used for pharmaceutical use as either the free base or a pharmaceutically acceptable acid addition salt thereof. Examples of the acid addition salts include inorganic acid addition salts such as hydrochloride, hydrobromide, nitrate, sulfate and phosphate; and organic acid addition salts such as formate, acetate, oxalate, fumarate, maleate, citrate, lactate, nicotinate, benzoate and methanesulfonate. The compound [I] of the present invention may be administered either orally or parenterally, and may be further used in conjunction or admixture with a pharmaceutical excipient which is suitable for oral or parenteral administration. The excipient selected must be one which does not react with the compound [I]. Suitable excipients include, for example, gelatin, lactose, glucose, sodium chloride, starch, magnesium stearate, talcum, vegetable oil and so forth. Other known medicinal excipients may be employed. The pharmaceutical preparation may be a solid dosage form such as a tablet, a coated tablet, a pill or a capsule, or a liquid dosage form such as a solution, a suspension or an emulsion. The pharmaceutical preparation may be sterilized and/or may contain auxiliaries such as preserving and stabilizing agents. The dose of the compound [I] for pharmaceutical use may vary dependent on the route of administration; the age, weight and condition of patients; and the particular disease to be treated. In general, it may be used for pharmaceutical use at a dose of 3 to 300 mg/kg, especially 10 to 100 mg/kg, per day.

Among the azepino[1,2,3-lm]-β-carboline compounds of the present invention, a preferred subgenus include the compound of the formula [I] in which $R^1$ is hydrogen, cycloalkyl of 6 or 7 carbon atoms, phenyl, hydroxy or acetyl. Another preferred subgenus include the compound of the formula [I] in which $R^1$ is cycloalkyl of 6 or 7 carbon atoms or phenyl, and A is single bond or methylene. Further preferred subgenus include 1,2,3,3a,4,5,6,7-octahydro-3-cycloheptyl-7-oxo-azepino[1,2,3-lm]-β-carboline, 1,2,3,3a,4,5,6,7-octahydro-3-cyclohexylmethyl-7-oxo-azepino[1,2,3-lm]-β-carboline and 1,2,3,3a,4,5,6,7-octahydro-3-benzyl-7-oxo-azepino[1,2,3-lm]-β-carboline.

According to the present invention, the compound [I] can be prepared by any one of the methods [A] through [I] described in the following schemes.

Method [A]

[II-a]

or

[II-b]

Intramolecular cyclization →

[I-a]

(In the above-mentioned reaction scheme, R[1]' is hydrogen, cycloalkyl of 3 to 7 carbon atoms or phenyl, R[2] is alkyl of one to 5 carbon atoms, and A' is straight or branched alkylene of one to 5 carbon atoms.)

Method [B]

[II-c]

Intramolecular cyclization →

[I-a]

(In the above-mentioned reaction scheme, R[1]' and A' are the same as defined above)

Method [C]

[III]

Intramolecular cyclization →

[IV]

Reduction →

[I-a]

(In the above-mentioned reaction scheme, R[3] is hydrogen or alkyl of one to 5 carbon atoms, and R[1]' and A' are the same as defined above.)

Method [D]

[I-b]

Catalytic hydrogenation →

[I-c]

Method [E]

[I-c]  +  X—A'—R[1]'''

[V]

→

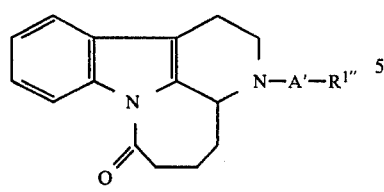

[I-d]

(In the above-mentioned reaction scheme, $R^{1'''}$ is hydrogen, cycloalkyl of 3 to 7 carbon atoms, phenyl, alkoxycarbonyl of 2 or 3 carbon atoms or alkanoyl of 2 or 3 carbon atoms, X is halogen, and A' is the same as defined above.)

Method [F]

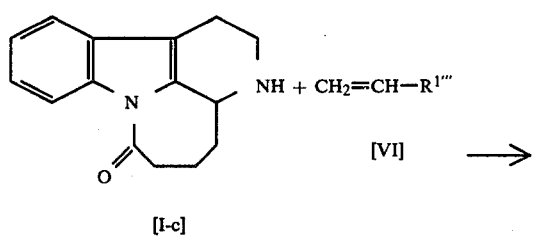

[I-c]

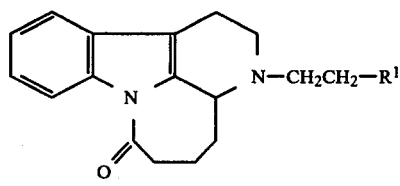

[I-e]

(In the above-mentioned reaction scheme, $R^{1''''}$ is alkoxycarbonyl of 2 or 3 carbon atoms or alkanoyl of 2 or 3 carbon atoms)

Method [G]

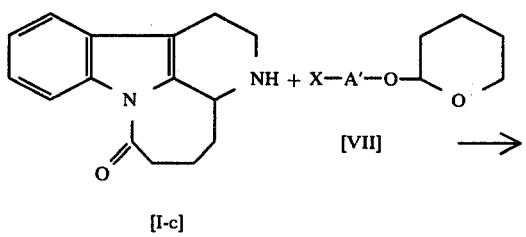

[I-c]

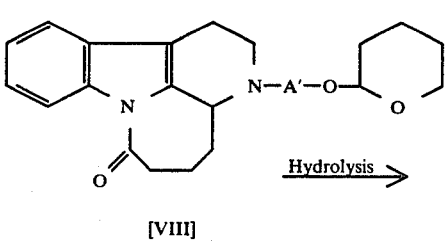

[VIII]

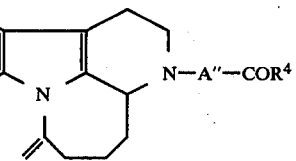

[I-f]

(In the above-mentioned reaction scheme, A' and X are the same as defined above.)

Method [H]

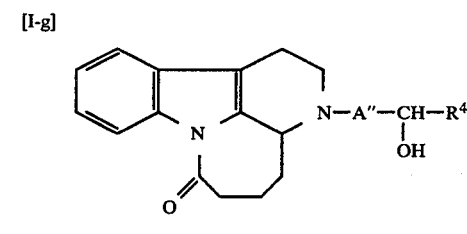

[I-g]

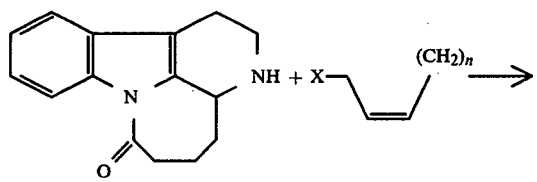

[I-h]

(In the above-mentioned reaction scheme, $R^4$ is alkyl of one or 2 carbon atoms, and A'' is alkylene of one to 3 carbon atoms.)

Method [I]

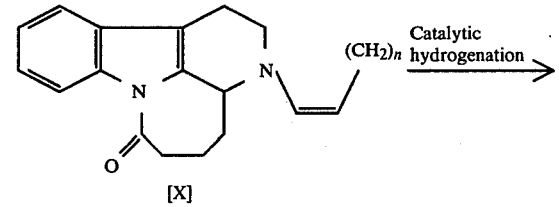

[I-c]  [IX]

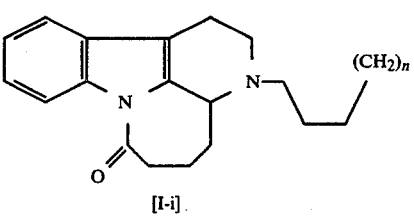

[X]

[I-i]

(In the above-mentioned reaction scheme, n is 3 or 4, and X is the same as defined above.)

The method [A] comprises intramolecular cyclization of a 1,2,3,4-tetrahydro-β-carboline compound [II-a] or [II-b] to give a 1,2,3,3a,4,5,6,7-octahydro-3-substituted-7-oxo-azepino[1,2,3-lm]-β-carboline compound [I-a]. The intramolecular cyclization of the compound [II-a] or [II-b] may be accomplished for example by treating it with acetic anhydride, trifluoroacetic acid, polyphosphoric acid, ethyl polyphosphate, phosphorous pentoxide or the like (e.g., Angew. Chem. Int. Ed. Egnl., Vol. 16, No. 12, pp 878–879(1977)). It is preferred to carry out the reaction at a temperature of 50° to 150° C. Moreover, the intramolecular cyclization of the compound [II-a] may be carried out in the presence of hexamethyldisilazane sodium salt (i.e., [(CH$_3$)$_3$Si]$_2$N-.Na), triphenylphosphine sodium salt, lithium diisopropylamine, sodium hydride, an alkali metal amine (e.g., sodium amide), an alkali metal alkoxide (e.g., sodium methoxide, sodium ethoxide, sodium tert.-amyloxide), 1,8-diazabicyclo[5,4,0]undecene-7 or 1,5-diazabicyclo[4,3,0]nonene-5. In the latter case, it is preferred to carry out the reaction at a temperature of 0° to 150° C. in an inert solvent. Examples of the solvent include benzene, toluene, xylene, ether, tetrahydrofuran, dioxane and dimethylformamide.

The method [B] comprises intramolecular cyclization of a 1,2,3,4-tetrahydro-1-carboxy-1-(3-carboxypropyl)-β-carboline compound [II-c] to give a 1,2,3,3a,4,5,6,7-octahydro-3-substituted-7-oxo-azepino[1,2,3-lm]-β-carboline compound [I-a]. The intramolecular cyclization of the compound [II-c] may be conducted for example by heating it in the presence of an acid, i.e., by heating the compound [II-c] and polyphosphoric acid until the intramolecular cyclization and decarboxylation are completed. It is preferred to carry out the reaction at a temperature of 50° to 150° C.

The method [C] comprises intramolecular cyclization of a N-acyl-tryptamine compound [III] to give a 1,2,4,5,6,7-hexahydro-3-substituted-7-oxo-azepino[1,2,3-lm]-β-carbolinium compound [IV], followed by reduction thereof to give a 1,2,3,3a,4,5,6,7-octahydro-3-substituted-7-oxo-azepino[1,2,3-lm]-β-carboline compound [I-a]. The intramolecular cyclization of the compound [III] may be accomplished for example by treating it with polyphosphoric acid, ethyl polyphosphate or trifluoroacetic acid. It is preferred to carry out the reaction at a temperature of 25° to 200° C., especially 120° to 150° C. The subsequent reduction of the compound [IV] is readily accomplished in a conventional manner. For example, the reaction may be carried out by treating the compound [IV] with a reducing agent in an inert solvent. An alkali metal borohydride (e.g., sodium borohydride, potassium borohydride, lithium borohydride), diborane and lithium aluminium alkoxy hydride (e.g., tri-tert.butoxyalumino hydride) are examples of suitable reducing agents. Suitable examples of the solvent include water, aqueous tetrahydrofuran, aqueous dioxane, acetonitrile, an alkanol (e.g., methanol, ethanol, propanol) and ethyl acetate. It is preferred to carry out the reaction at a temperature of −10° to 50° C. Alternatively, the reduction reaction may be carried out for example by catalytic hydrogenation of the compound [IV] in the presence of a catalyst in an inert solvent. Platinum dioxide, palladiumblack, palladium-carbon and the like are examples of suitable catalysts. Examples of the solvent include an alkanol (e.g., methanol, ethanol, propanol), acetic acid and a mixture of said alkanol and water.

The method [D] comprises the step of catalytic hydrogenation of 1,2,3,3a,4,5,6,7-octahydro-3-benzyl-7-oxo-azepino[1,2,3-lm]-β-carboline [I-b] (i.e., the compound [I] in which A is methylene and R$^1$ is phenyl) to give 1,2,3,3a,4,5,6,7-octahydro-7-oxo-azepino[1,2,3-lm]-β-carboline [I-c]. The catalytic hydrogenation of the compound [I-b] may be carried out for example in the presence of a catalyst in a hydrogen atmosphere. It is preferred to carry out the reaction in the presence of an acid (e.g., hydrochloric acid, hydrobromic acid, acetic acid). It is also preferred to carry it out at a temperature of 20° to 50° C. Examples of the catalyst include palladium-carbon, palladium-barium carbonate, colloidal palladium and the like. An alkanol (e.g., methanol, ethanol, propanol) or a mixture of said alkanol and water are suitable as the reaction solvent.

The method [E] comprises reacting 1,2,3,3a,4,5,6,7-octahydro-7-oxo-azepino[1,2,3-lm]-β-carboline [I-c] (i.e., the compound [I] in which A is single bond and R$^1$ is hydrogen) with a halide compound [V] to give a 1,2,3,3a,4,5,6,7-octahydro-3-substituted-7-oxo-azepino[1,2,3-lm]-β-carboline compound [I-d]. The reaction of the compound [I-c] with the compound [V] may be carried out for example in the presence of an acid acceptor in an inert solvent. Examples of said acid acceptor include sodium hydride, an alkali metal amide (e.g., sodium amide, potassium amide), an alkali metal carbonate (e.g., potassium carbonate, sodium carbonate), an alkali metal alkoxide (e.g., sodium methoxide, sodium ethoxide, sodium tert.amyloxide), an organic base (e.g., pyridine, collidine, N-dimethylaniline, triethylamine). Examples of the solvent include acetonitrile, dimethylformamide, dimethylsulfoxide, acetone, ethyl acetate and an alkanol (e.g., methanol, ethanol, propanol). It is preferred to carry out the reaction at a temperature of 0° to 150° C.

The method [F] comprises reacting 1,2,3,3a,4,5,6,7-octahydro-7-oxo-azepino[1,2,3-lm]-β-carboline [I-c] with a vinyl compound [VI] to give a 1,2,3,3a,4,5,6,7-octahydro-3-substituted-7-oxo-azepino[1,2,3-lm]-β-carboline compound [I-e]. The reaction of the compound [I-c] with the compound [VI] may be carried out for example by stirring a mixture of said compounds at a temperature of −5° to 150° C. It is preferred to carry out the reaction in the presence of a small amount of an acid (e.g., formic acid, acetic acid, trifluoroacetic acid, borontrifluoride-etherate, p-toluenesulfonic acid, sulfuric acid, hydrochloric acid, hydrobromic acid, methanesulfonic acid).

The method [G] comprises reacting 1,2,3,3a,4,5,6,7-octahydro-7-oxo-azepino[1,2,3-lm]-β-carboline [I-c] with a O-(tetrahydropyran-2-yl)-hydroxyalkyl halide compound [VII] to give a 1,2,3,3a,4,5,6,7-octahydro-3-[O-(tetrahydropyran-2-yl)-hydroxyalkyl]-7-oxo-azepino[1,2,3-lm]-β-carboline compound [VIII], followed by hydrolysis thereof to give a 1,2,3,3a,4,5,6,7-octahydro-3-hydroxyalkyl-7-oxo-azepino[1,2,3-lm]-β-carboline compound [I-f]. The reaction of the compound [I-c] with the compound [VII] may be conducted in the same manner as described in the method [E]. The subsequent hydrolysis of the compound [VIII] may be carried out for example by treating it with an acid in an inert solvent. Examples of the acid include hydrochloric acid, hydrobromic acid and sulfuric acid. A mixture of water and an alkanol (e.g., methanol, ethanol, propanol) is suitable as the solvent. It is preferred to carry out the reaction at a temperature of 0° to 100° C.

The method [H] comprises reducing a 1,2,3,3a,4,5,6,7-octahydro-3-alkanoylalkyl-7-oxo-azepino[1,2,3-lm]-β-carboline compound [I-g] (e.g., the compound [I] in which A is straight or branched alkylene of one to 3 carbon atoms and R¹ is alkanoyl of 2 or 3 carbon atoms) to give a 1,2,3,3a,4,5,6,7-octahydro-3-hydroxyalkyl-7-oxo-azepino[1,2,3-lm]-β-carboline compound [I-h]. The reduction reaction of the compound [I-g] may be carried out for example by treating it with a reducing agent in an inert solvent. An alkali metal borohydride (e.g., sodium borohydride, potassium borohydride, lithium borohydride), lithium aluminum alkoxy hydride (e.g., lithium tri-tert.butoxy alumino hydride) are example of suitable reducing agents. Suitable examples of the solvent include an alkanol (e.g., methanol, ethanol, propanol, tert.-amylalcohol), ether, tetrahydrofurane, dioxane, and a mixture thereof. It is preferred to carry out the reaction at a temperature of −10° to 50° C.

The method [I] comprises reacting 1,2,3,3a,4,5,6,7-octahydro-7-oxo-azepino[1,2,3-lm]-β-carboline [I-c] with a cycloalkenyl halide compound [IX] to give a 1,2,3,3a,4,5,6,7-octahydro-3-cycloalkenyl-7-oxo-azepino[1,2,3-lm]-β-carboline compound [X], followed by catalytic hydrogenation thereof to give a 1,2,3,3a,4,5,6,7-octahydro-3-cycloalkyl-7-oxo-azepino-[1,2,3-lm]-β-carboline compounds [I-i]. The reaction of the compounds [I-c] and [IX] may be conducted in the same manner as described in the method [E[. The subsequent catalytic hydrogenation of the compound [X] may be carried out for example in the presence of a catalyst in a hydrogen atmosphere under neutral or acidic conditions. Suitable examples of the catalyst include palladium-carbon, palladium-black, palladium-barium carbonate, palladium-calcium carbonate, colloidal palladium, Raney nickel and platinum dioxide. An alkanol (e.g., methanol, ethanol, propanol), ethyl acetate and acetic acid are examples of suitable solvents. It is preferred to carry out the reaction at a temperature of 20° to 150° C.

The compound [I] of the present invention thus obtained may be, if required, further converted to a pharmaceutically acceptable acid addition salt thereof. Said salt may be prepared by simple neutralization of the compound [I] in the form of free base with an acid in a solvent such as an alkanol (e.g., methanol, ethanol, propanol), ether, isopropyl ether, tetrahydrofurane, dioxane, acetone, water or a mixture thereof.

The starting compounds of the present invention, i.e., the compounds [II-a], [II-b], [II-c] and [III], may be prepared by any one of the methods [J] through [R] described in the following reaction schemes.

Method [J]

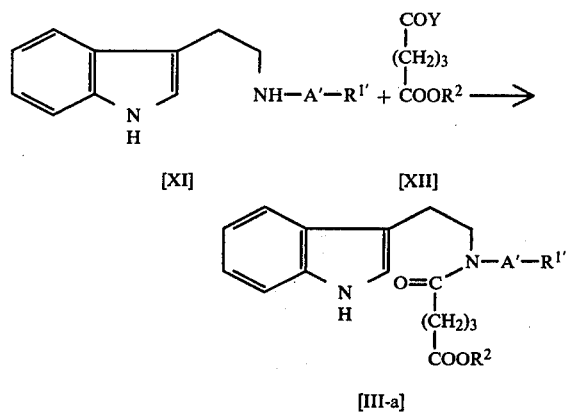

Method [K]

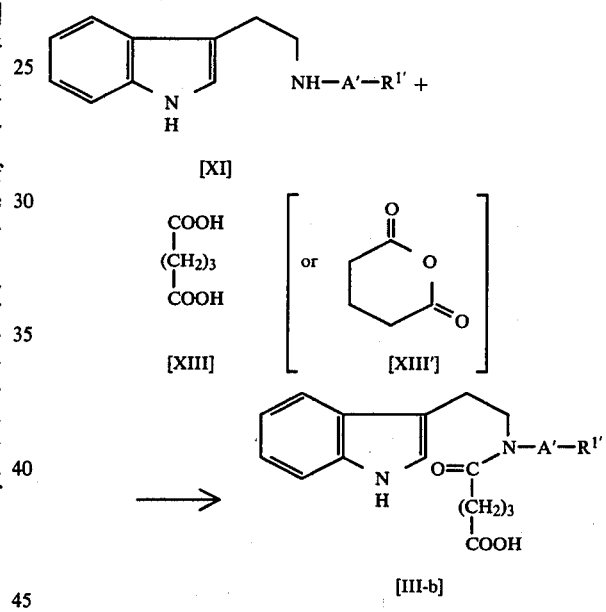

Method [L]

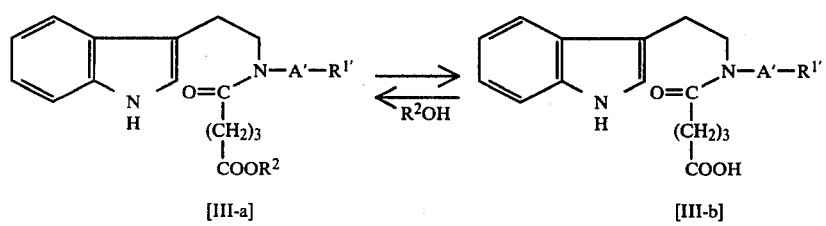

Method [M]
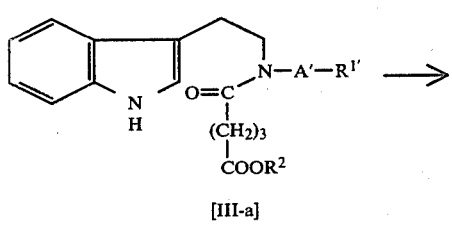
Method [N]
Method [O]
-continued
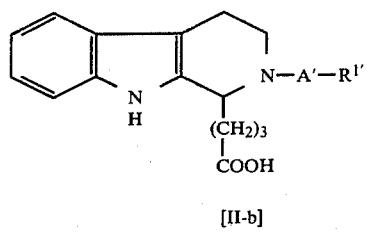
Method [P]
Method [Q]
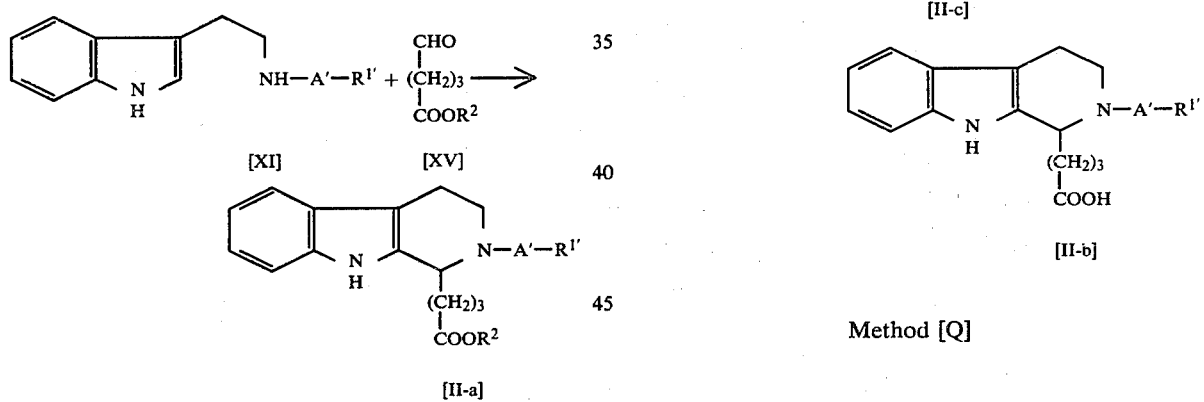
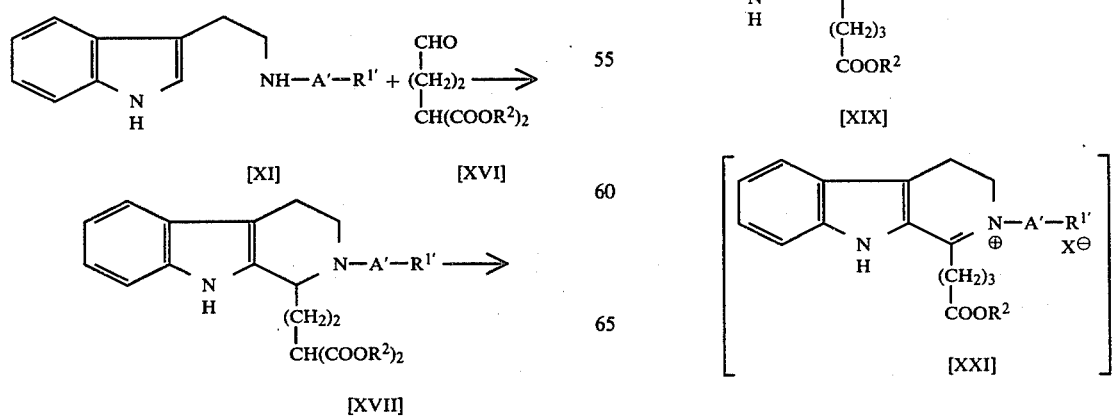

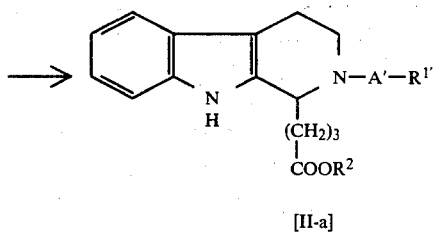

[II-a]

Method [R]

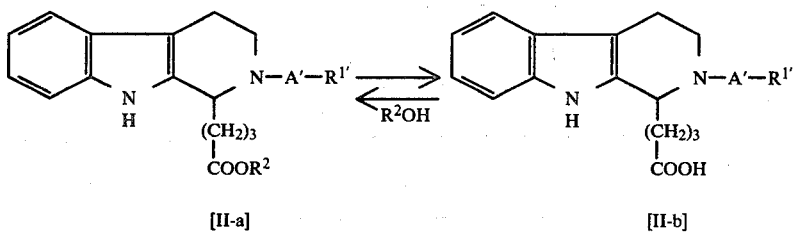

[II-a]　　　　　　　　　　[II-b]

(In the above-mentioned reaction schemes, Y is halogen, hydroxy or alkoxy of one to 6 carbon atoms, and $R^{1'}$, $R^2$, $A'$ and X are the same as defined above.)

The reaction of the method [J], i.e., the acylation reaction of a tryptamine compound [XI] with a glutaric acid derivative [XII] (Y=halogen), may be accomplished by conventional methods of the Schotten-Baumann reaction. For example, it is carried out at a temperature between $-10°$ C. and $50°$ C. in the presence of an acid acceptor (e.g., pyridine, collidine, triethylamine, sodium hydroxide, sodium carbonate, sodium bicarbonate) in a solvent (e.g., benzene, toluene, ethyl acetate, acetonitrile, ether, tetrahydrofuran, acetone, methylenedichloride, chloroform, dimethylformamide). When pyridine or collidine is used as the acid acceptor, however, it is not always necessary to use the solvent because said organic acid acceptor serves as the solvent. Alternatively, the compound [III-a] may be obtained by heating the compounds [XI] and [XII] (Y=alkoxy) at a temperature of $100°$ to $200°$ C. Moreover, the compound [III-a] may be obtained by reacting a glutaric acid derivative [XIII] (Y=OH) with methyl chloroformate, ethyl chloroformate, butyl chloroformate, isobutyl chloroformate, amyl chloroformate, benzyl chloroformate, p-methylbenzyl chloroformate, p-chlorobenzyl chloroformate, p-methoxybenzyl chloroformate, pivalyl chloride, pentachlorophenol, chloroacetonitrile, N-hydroxysuccinimide or N-hydroxyphthalimide, and then reacting the resultant mixed anhydride or activated ester of the compound [XII] with the compound [XI].

The reaction of the method [K], i.e., the acylation reaction of a tryptamine compound [XI] with glutaric acid [XIII] or its anhydride [XIII'], is readily accomplished by heating the compounds [XI] and [XIII] (or [XIII']) at a temperature between $80°$ C. and $200°$ C. If required, the reaction may be carried out in an inert solvent such as benzene, toluene, xylene or dioxane.

The hydrolysis of a N-(4-alkoxycarbonylbutyryl)-tryptamine compound [III-a] in the method (L) may be carried out by treating it at $0°$ to $50°$ C. with an alkali (e.g., sodium hydroxide, potassium hydroxide, sodium carbonate, sodium bicarbonate, potassium carbonate) in an inert solvent (e.g., aqueous methanol, aqueous ethanol, aqueous propanol). On the other hand, the esterification of a N-(4-carboxybutyryl)-tryptamine compound [III-b] may be conducted for example by reacting said compound with an alkanol (e.g., methanol, ethanol, propanol) at $0°$ to $120°$ C. in the presence of an acid (e.g., p-toluene-sulfonic acid, hydrochloric acid, sulfuric acid) or thionyl chloride.

With respect to the method [M], the intramolecular cyclization of a N-(4-alkoxycarbonylbutyryl)-tryptamine compound [III-a] may be carried out for example by treating said compound with phosphorus oxychloride, phosphorus oxybromide, phosphorus pentachloride, polyphosphoric acid or ethyl polyphosphate at $30°$ to $150°$ C. in a solvent (e.g., acetonitrile, benzene, toluene, xylene, chloroform, pyridine). When phosphorus oxychloride or phosphorus oxybromide is used, however, it is not always necessary to use the solvent because said agent serves as the solvent. The subsequent reduction of a 3,4-dihydro-1-(3-alkoxycarbonylpropyl)-β-carbolinium compound [XIV] thus obtained may be carried out for example by treating it with a reducing agent (e.g., sodium borohydride, potassium borohydride, lithium borohydride, diborane, lithium tri-tert. butoxyalumino hydride) at $-10°$ to $50°$ C. in an inert solvent (e.g., water, aqueous tetrahydrofuran, aqueous dioxane, acetonitrile, methanol, ethanol, propanol, ethyl acetate). Alternatively, said reduction reaction may be carried out for example by catalytic hyrogenation of the compound [XIV] at $20°$ to $60°$ C. in the presence of a catalyst (e.g., platinum dioxide, palladium-black, palladium-carbon and the like) in an inert solvent (e.g., methanol, ethanol, propanol, acetic acid, a mixture of said alkanol and water).

The reaction of a tryptamine compound [XI] with a 4-alkoxycarbonylbutyraldehyde [XV], i.e., the method [N], may be carried out at $20°$ to $150°$ C. in the presence of an acid (e.g., p-toluenesulfonic acid, acetic acid, hydrochloric acid, sulfuric acid, phosphoric acid), thionyl chloride or a Lewis acid (e.g., trifluoroborane) in an inert solvent (e.g., methanol, ethanol, propanol, acetonitrile, benzene, toluene, xylene, chloroform, ether). Alternatively, the reaction may be carried out at $-10°$ to $50°$ C. under mild alkaline conditions, i.e., at a pH of 7 to 10, in the presence of an alkali metal hydroxide (e.g., sodium hydroxide, potassium hydroxide) or an alkali metal carbonate (e.g., sodium carbonate, potassium carbonate, sodium bicarbonate) in an inert solvent (e.g., methanol, ethanol, tetrahydrofuran, dioxane, dimethylformamide, water).

The reaction of a tryptamine compound [XI] with a 4,4-bis(alkoxycarbonyl)butyraldehyde [XVI], i.e., the method [O], may be conducted for example in the same manner as described in the method [N], and the subsequent decarboxylation of a 1,2,3,4-tetrahydro-1-[3,3-bis-(alkoxycarbonyl)propyl]-β-carboline compound [XVII] may be readily accomplished for example by dissolving the compound [XVII] in a mixture of acetic acid and hydrochloric acid, and heating the mixture at a temperature of 50° to 150° C. until the decarboxylation reaction is completed.

The method [P], i.e., the reaction of a tryptamine compound [XI] with α-keto-adipic acid [XVIII], may be conducted for example in a conventional manner such as those described in J. Med. Chem., Vol. 7, pp 135–141(1964), Chem, Ber., Vol. 71, pp 2163–2175(1938) or Heterocycles, Vol. 6, pp 1101–1105(1976). For example, the starting compunds [XI] and [XVIII] are dissolved in an inert solvent, and the mixture is heated at a temperature of 50° and 150° C. Suitable examples of the solvent include benzene, dioxane, toluene, xylene, tetrahydrofuran and a mixture thereof. The resultant compounds [II-c] and [II-b] are separated from each other by recrystallization.

The method [Q] comprises reacting a 3,4-dihydro-1-(3-alkoxycarbonylpropyl)-β-carboline compound [XIX] with an halide compound [XX] to give a 3,4-dihydro-1-(3-alkoxycarbonylpropyl)-β-carbolinium compound [XXI], and then reducing the compound [XXI]. The reaction of the 3,4-dihydro-1-(3-alkoxycarbonylpropyl)-β-carboline compound [XIV] with the halide compound [XX] may be readily carried out for example by stirring a mixture of these compounds at a temperature of 20° to 150° C. in a solvent (e.g., benzene, toluene, ethyl acetate, chloroform, methanol, ethanol, propanol, acetone, acetonitrile). Moreover, the subsequent reduction reaction of the 3,4-dihydro-1-(3-alkoxycarbonylpropyl)-β-carbolinium compound [XXI] may be conducted in the same manner as described in the method [M].

The method [R], i.e., the hydrolysis and esterification, may for example be conducted in the same manner as described in the method [L].

EXPERIMENT (Anti-anoxic activity)

A suspension of a test compound in 0.5% carboxymethyl cellulose was administered intraperitoneally to a group of male mice weighing about 20 g (one group consisting of 10 mice). Fifteen minutes after administration of the test compound, the mice were placed in an atmosphere impoverished in oxygen by creating a partial vacuum (165 mm Hg). The survival time of the mice was measured with a chronometer. Then, $SD_{50}$ (i.e., the dose required to produce 50% increase in the survival time of mice as compared with that of a group of non-medicated mice) was calculated from the dose-response curve obtained by regression equation.

(Test compounds)

| Compound Nos. | Chemical name |
|---|---|
| | (The compounds of the present invention) |
| 1. | 1,2,3,3a,4,5,6,7-octahydro-7-oxo-azepino-[1,2,3-lm]-β-carboline hydrochloride |
| 2. | 1,2,3,3a,4,5,6,7-octahydro-3-methyl-7-oxo-azepino[1,2,3-lm]-β-carboline hydrochloride |
| 3. | 1,2,3,3a,4,5,6,7-octahydro-3-ethyl-7-oxo-azepino[1,2,3-lm]-β-carboline hydrochloride |
| 4. | 1,2,3,3a,4,5,6,7-octahydro-3-n-propyl-7-oxo-azepino[1,2,3-lm]-β-carboline hydrochloride |
| 5. | 1,2,3,3a,4,5,6,7-octahydro-3-n-pentyl-7-oxo-azepino[1,2,3-lm]-β-carboline hydrochloride |
| 6. | 1,2,3,3a,4,5,6,7-octahydro-3-cycloheptyl-7-oxo-azepino[1,2,3-lm]-β-carboline hydrochloride |
| 7. | 1,2,3,3a,4,5,6,7-octahydro-3-cyclohexylmethyl-7-oxo-azepino[1,2,3-lm]-β-carboline hydrochloride |
| 8. | 1,2,3,3a,4,5,6,7-octahydro-3-benzyl-7-oxo-azepino[1,2,3-lm]-β-carboline hydrochloride |
| 9. | 1,2,3,3a,4,5,6,7-octahydro-3-(2-acetylethyl)-7-oxo-azepino[1,2,3-lm]-β-carboline hydrochloride |
| 10. | 1,2,3,3a,4,5,6,7-octahydro-3-(2-hydroxyethyl)-7-oxo-azepino[1,2,3-lm]-β-carboline hydrochloride |
| 11. | 1,2,3,3a,4,5,6,7-octahydro-3-(2-hydroxy-n-propyl)-7-oxo-azepino[1,2,3-lm]-β-carboline hydrochloride |
| (The known compound) | |
| 12. | vincamine (free base) |

(Results)

The results are shown in the following Table.

Table

| Compound Nos. | Dose (mg/kg) | Anti-anoxic activity Survival time mean ± S.E. (second) | $SD_{50}$ (mg/kg) |
|---|---|---|---|
| 1. | 10 | 91.7 ± 4.57 | |
| | 15 | 156.3 ± 12.80 | 8.9 |
| | 20 | 190.0 ± 20.27 | |
| | 30 | 198.8 ± 19.38 | |
| 2. | 3 | 63.9 ± 1.99 | |
| | 10 | 139.4 ± 13.11 | 4.7 |
| | 20 | 197.6 ± 19.22 | |
| 3. | 7 | 81.2 ± 10.76 | |
| | 10 | 118.7 ± 8.23 | 7.7 |
| | 20 | 165.3 ± 14.61 | |
| | 30 | 179.0 ± 20.86 | |
| 4. | 10 | 84.9 ± 6.38 | |
| | 30 | 160.7 ± 12.85 | 11.2 |
| | 100 | 235.3 ± 22.14 | |
| 5. | 10 | 84.7 ± 9.42 | |
| | 20 | 93.3 ± 11.39 | 13.3 |
| | 30 | 149.1 ± 20.66 | |
| | 100 | 187.1 ± 15.39 | |
| 6. | 30 | 136.7 ± 9.87 | |
| | 60 | 159.1 ± 9.30 | 7.39 |
| | 100 | 174.7 ± 11.1 | |
| 7. | 10 | 80.1 ± 7.05 | |
| | 30 | 124.2 ± 17.87 | 14.1 |
| | 100 | 201.9 ± 17.31 | |
| 8. | 10 | 61.7 ± 5.89 | |
| | 30 | 92.7 ± 9.65 | 21.1 |
| | 100 | 185.6 ± 20.45 | |
| 9. | 10 | 84.4 ± 6.35 | |
| | 30 | 116.6 ± 17.57 | 13.9 |
| | 60 | 199.7 ± 20.37 | |
| | 100 | 211.7 ± 16.83 | |
| 10. | 10 | 85.3 ± 7.00 | |
| | 30 | 113.9 ± 12.33 | 13.6 |
| | 60 | 188.5 ± 20.22 | |
| 11. | 10 | 78.1 ± 5.79 | |
| | 30 | 138.0 ± 15.34 | 12.7 |
| | 60 | 163.5 ± 20.34 | |
| | 100 | 171.9 ± 11.53 | |
| (Known compound) | 10 | 67.2 ± 3.65 | |
| | 20 | 96.2 ± 6.69 | |
| 12. vincamine | 30 | 105.3 ± 10.20 | |
| | 70 | 86.8 ± 5.46 | |
| | 150 | 60.1 ± 5.41 | |

Practical and presently preferred embodiments of the present invention are illustratively shown in the following examples.

EXAMPLE 1

10 g of N-ethyl-tryptamine (i.e., 3-(2-ethylaminoethyl)-indole) were dissolved in 80 ml of pyridine, and 9.62 g of 4-methoxycarbonylbutyryl chloride were added dropwise thereto at 10° C. The mixture was stirred for one hour. After the reaction was completed, the mixture was acidified with dilute hydrochloric acid and then extracted with ethyl acetate. The extract was washed with water, an aqueous saturated sodium bicarbonate solution and water, successively. The washed extract was dried and evaporated under reduced pressure to remove solvent. The oily residue thus obtained was recrystallized from a mixture of ethanol and petroleum ether. 12.5 g of N-ethyl-N-(4-methoxycarbonylbutyryl)-tryptamine (i.e., 3-[2-(N-ethyl-4-methoxycarbonylbutanamido)ethyl]-indole]were thereby obtained as yellow crystals. M.p. 73°-75° C. Yield: 74.4%

IR$\nu_{max}^{Nujol}$ (cm$^{-1}$): 3220, 1730, 1615, 735

Mass (m/e): 316(M+)

NMR ($\delta$, CDCl$_3$): 8.50-8.10 (broad, 1H, >NH); 7.80-6.90 (m, 5H, aromatic); 3.70 (s, 3H, COCH$_3$); 1.16 (t, 3H, >NCH$_2$CH$_3$)

EXAMPLE 2

10.3 g of N-methyl-tryptamine (i.e., 3-(2-methylaminoethyl)-indole) and 11.7 g of 4-methoxycarbonylbutyryl chloride were treated in the same manner as described in Example 1. 16.6 g of N-methyl-N-(4-methoxycarbonylbutyryl)-tryptamine (i.e., 3-[2-(N-methyl-4-methoxycarbonylbutanamido)ethyl]indole) were therby obtained. Yield: 92.8%

M.p. 101°-102° C. (recrystallized from a mixture of ethyl acetate and n-hexane)

IR$\nu_{max}^{Nujol}$ (cm$^{-1}$): 3225, 1732, 1610

Mass (m/e): 302 (M+)

NMR ($\delta$, CDCl$_3$): 8.3-8.0 (broad, 1H, >NH); 7.9-6.83 (m, 5H, aromatic); 3.66 (s, 3H, COOCH$_3$); 2.98 (s, 3H, >NCH$_3$)

EXAMPLE 3

10 g of N-isobutyl-tryptamine (i.e., 3-(2-isobutylaminoethyl)-indole) and 9.1 g of 4-methoxycarbonylbutyryl chloride were treated in the same manner as described in Example 1. 11.23 g of N-isobutyl-N-(4-methoxycarbonylbutyl)-tryptamine (i.e., 3-[2-(N-isobutyl-4-methoxycarbonylbutanamido)ethyl]-indole) were thereby obtained. Yield: 70.5%

M.p. 103°-104° C. (recrystallized from a mixture of benzene and isopropyl ether)

IR$\nu_{max}^{Nujol}$ (cm$^{-1}$): 3210, 1730, 1610, 745

Mass (m/e): 344 (M+)

NMR ($\delta$, CDCl$_3$): 8.50 (broad, 1H, >NH); 7.8-7.0 (m, 5H, aromatic); 3.66 (s, 3H, COOCH$_3$); 0.87 (d, 6H, —CH(CH$_3$)$_2$)

EXAMPLE 4

(1) 10.0 g of tryptamine were dissolved in a mixture of 10 ml of pyridine and 100 ml of chloroform, and 9.9 g of n-valeryl chloride were added dropwise thereto at 10° C. under cooling with ice-water. The mixture was stirred at the same temperature for one hour. After the reaction was completed, the mixture was poured into about 100 ml of ice-water. Then, the aqueous mixture was extracted with chloroform, and the extract was washed with water, 10% hydrochloric acid and water, successively. The washed extract was dried and evaporated to remove solvent. The residue thus obtained was recrystallized from n-hexane. 13.9 g of N-n-valeryl-tryptamine (i.e., 3-(2-n-pentanamidoethyl)-indole) were thereby obtained. M.p. 86°-87° C. Yield: 92.1%

IR$\nu_{max}^{Nujol}$ (cm$^{-1}$): 3400, 3260, 1630

Mass (m/e): 244 (M+)

NMR ($\delta$, CDCl$_3$): 8.60 (broad, 1H, >NH) 7.70-6.8 (m, 5H, aromatic); 5.7 (broad, 1H, —NHCO—)

(2) 13.9 g of N-n-valeryl-tryptamine were dissolved in 50 ml of absolute tetrahydrofuran, and a suspension of 4.3 g of lithium aluminium hydride in 150 ml of absolute tetrahydrofuran was added dropwise thereto at room temperature. The mixture was refluxed for 16 hours. After the reaction was completed, water and tetrahydrofuran were added to the mixture. Insoluble materials were removed by filtration, and the filtrate was evaporated under reduced pressure to remove solvent. 13.1 g of N-pentyl-tryptamine (i.e., 3-(2-pentylaminoethyl)-indole) were thereby obtained as an oil. Yield: 100%

IR$\nu_{max}^{film}$ (cm$^{-1}$): 3420

Mass (m/e): 230 (M+)

NMR ($\delta$, CDCl$_3$): 8.33 (broad, 1H, >NH); 7.63-6.82 (m, 5H, aromatic); 3.63 (m, 1H, -NH-)

Hydrochloride:

M.p. 197°-198° C. (recrystallized from a mixture of ethanol and ether)

IR$\nu_{max}^{Nujol}$ (cm$^{-1}$): 3420, 2800-2300

(3) 13.4 g of N-pentyl-tryptamine and 10.5 g of 4-methoxycarbonylbutyryl chloride were treated in the same manner as described in Example 1. 14.9 g of N-pentyl-N-(4-methoxycarbonylbutyryl)-tryptamine (i.e., 3-[2-(N-pentyl-4-methoxycarbonylbutanamido)ethyl]-indole) were thereby obtained. Yield: 71.9%

M.p. 70°-71° C. (recrystallized from isopropyl ether)

IR$\nu_{max}^{Nujol}$ (cm$^{-1}$): 3200, 1735, 1610

Mass (m/e): 358 (M+)

NMR ($\delta$, CDCl$_3$): 8.42 (broad, 1H, >NH); 7.79-6.89 (m, 5H, aromatic); 3.66 (s, 3H, COOCH$_3$)

EXAMPLE 5

10.5 g of N-cyclopropylmethyl-tryptamine (i.e., 3-(2-cyclopropylmethylaminoethyl)-indole) and 9.7 g of 4-methoxycarbonylbutyryl chloride were treated in the same manner as described in Example 1. 10.1 g of N-cyclopropylmethyl-N-(4-methoxycarbonylbutyryl)-tryptamine (i.e., 3-[2-(N-cyclopropylmethyl-4-methoxycarbonylbutanamido)ethyl]-indole) were thereby obtained. Yield: 60.3%

M.p. 99°-100° C. (recrystallized from a mixture of benzene and isopropyl ether)

IR$\nu_{max}^{Nujol}$ (cm$^{-1}$): 3220, 1730, 1615, 740

Mass (m/e): 342 (M+)

NMR ($\delta$, CDCl$_3$): 8.55 (broad, 1H, L22 NH); 7.8-7.0 (m, 5H, aromatic); 3.66 (s, 3H, COOCH$_3$); 1.4-0.1 (m, 5H, )

EXAMPLE 6

(1) 10 g of tryptamine and 10 g of cyclohexylcarbonyl chloride were treated in the same manner as described in Example 4-(1). 13.7 g of N-cyclohexylcarbonyl-tryptamine (i.e., 3-(2-cyclohexylcarbonylaminoethyl)-indole) were thereby obtained. Yield: 81.2%

M.p. 98°-99° C. (recrystallized from n-hexane)

IR$\nu_{max}^{Nujol}$ (cm$^{-1}$): 1620

Mass (m/e): 270 (M+)

NMR ($\delta$, CDCl$_3$): 8.5 (broad, 1H, >NH); 7.7-6.8 (m, 5H, aromatic); 5.6 (broad, 1H,

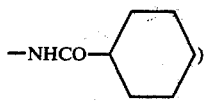

(2) 13.7 g of N-cyclohexylcarbonyl-tryptamine were treated in the same manner as described in Example 4-(2). 12.1 g of N-cyclohexylmethyl-tryptamine (i.e., 3-(2-cyclohexylmethylaminoethyl)-indole) were thereby obtained as an oil. Yield: 93.8%

IR$\nu_{max}^{film}$ (cm$^{-1}$): 3320
Mass (m/e): 256 (M+)
NMR (δ, CDCl$_3$): 8.49 (broad, 1H, >NH) 7.69–6.90 (m, 5H, aromatic) 3.68 (s, 1H, -NH-)
Hydrochloride:
M.p. 202°–203° C. (recrystallized from a mixture of ethanol and ether)
IR$\nu_{max}^{Nujol}$ (cm$^{-1}$): 3325, 1580

(3) 12.0 g of N-cyclohexylmethyl-tryptamine and 8.47 g of 4-methoxycarbonylbutyryl chloride were treated in the same manner as described in Example 1. 15.2 g of N-cyclohexylmethyl-N-(4-methoxycarbonylbutyryl)-tryptamine (i.e., 3-[2-(N-cyclohexylmethyl-4-methoxycarbonylbutanamido)-ethyl]-indole) were thereby obtained. Yield: 84.9%
M.p. 102°–103° C. (recrystallized from isopropyl ether)
IR$\nu_{max}^{Nujol}$ (cm$^{-1}$): 3200, 1720, 1600
Mass (m/e): 384 (M+)
NMR (δ, CDCl$_3$): 8.30 (broad, 1H, >NH); 7.70–6.93 (m, 5H, aromatic); 3.66 (s, 3H, COOCH$_3$)

EXAMPLE 7

42.8 g of N-benzyl-tryptamine (i.e., 3-(2-benzylaminoethyl)-indole) and 35.0 g of 4-methoxycarbonylbutyryl chloride were treated in the same manner as described in Example 1. 42.0 g of N-benzyl-N-(4-methoxycarbonylbutyryl)-tryptamine (i.e., 3-[2-(N-benzyl-4-methoxycarbonylbutanamido)ethyl]-indole) were thereby obtained. Yield: 75.0%
M.p. 107°–108.5° C. (recrystallized from a mixture of benzene and isopropyl ether)
IR$\nu_{max}^{Nujol}$ (cm$^{-1}$): 3180, 1730, 1630, 730
Mass (m/e): 378 (M+)
NMR (δ, CDCl$_3$): 8.11 (broad, s, 1H, >NH) 4.62–4.39 (2H, >NCH$_2$—ph)

EXAMPLE 8

8.0 g of dimethyl glutarate were added to 8.70 g of N-methyl-tryptamine (i.e., 3-(2-methylaminoethyl)-indole), and the mixture was heated at 150° C. under reduced pressure for 2 hours. After the reaction was completed, the mixture was acidified with dilute hydrochloric acid and then extracted with ethyl acetate. The extract was washed with water, an aqueous saturated sodium bicarbonate solution and an aqueous saturated sodium chloride solution, successively. The washed extract was dried and evaporated under reduced pressure to remove solvent. The residue thus obtained was recrystallized from a mixture of ethyl acetate and n-hexane. 11.3 g of N-methyl-N-(4-methoxycarbonylbutyryl)-tryptamine (i.e., 3-[2-(N-methyl-4-methoxycarbonylbutanamido)ethyl]-indole) were thereby obtained. M.p. 101°–102° C. Yield: 70%

EXAMPLE 9

8.70 g of N-methyl-tryptamine (i.e., 3-(2-methylaminoethyl)-indole) were dissolved in 100 ml of benzene, and 5.7 g of glutaric acid anhydride were added thereto. The mixture was stirred at 80° C. for 3 hours. After the reaction was completed, the mixture was evaporated to remove solvent. 12.0 g of N-methyl-N-(4-carboxybutyryl)-tryptamine (i.e., 3-[2-(N-methyl-4-carboxybutanamido)ethyl]-indole) were thereby obtained. Yield: 90%
M.p. 125°–126° C. (recrystallized from a mixture of ethyl acetate and n-hexane)
IR$\nu_{max}^{Nujol}$ (cm$^{-1}$): 3220, 1700
Mass (m/e): 288 (M+)

EXAMPLE 10

6.6 g of glutaric acid were added to 8.70 g of N-methyl-tryptamine (i.e., 3-(2-methylaminoethyl)-indole), and the mixture was heated at 150° C. under reduced pressure for 2 hours. After the reaction was completed, the product was recrystallized from a mixture of ethyl acetate and n-hexane. 10.8 g of N-methyl-N-(4-carboxybutyryl)-tryptamine (i.e., 3-[2-(N-methyl-4-carboxybutanamido)ethyl]-indole) were thereby obtained. M.p. 125°–126° C. Yield: 75.0%

EXAMPLE 11

1.5 ml of an aqueous 10% sodium hydroxide solution and 10 ml of a mixture of methanol and water (1:1) were added to 0.63 g of N-isobutyl-N-(4-methoxycarbonylbutyryl)-tryptamine (i.e., 3-[2-(N-isobutyl-4-methoxycarbonylbutanamido)ethyl]-indole). The mixture was stirred at 60° C. for 30 minutes. After the reaction was completed, the mixture was evaporated to remove solvent. The residue thus obtained was adjusted to a pH of 2.0 with 10% hydrochloric acid, and then extracted with chloroform. The extract was washed with water and concentrated. 0.6 g of N-isobutyl-N-(4-carboxybutyryl)-tryptamine (i.e., 3-[2-(N-isobutyl-4-carboxybutanamido)ethyl]-indole) were thereby obtained. Yield: 99.3%
M.p. 140°–141° C. (recrystallized from ethyl acetate)
IR$\nu_{max}^{Nujol}$ (cm$^{-1}$): 3220, 1700
Mass (m/e): 330 (M+)

EXAMPLE 12

30 ml of methanol and 10 mg of p-toluenesulfonic acid were added to 2.88 g of N-methyl-N-(4-carboxybutyryl)-tryptamine (i.e., 3-[2-(N-methyl-4-carboxybutanamido)ethyl]-indole). The mixture was refluxed for 5 hours. After the reaction was completed, the mixture was concentrated to about 10 ml. The concentrated mixture was diluted with an aqueous saturated sodium bicarbonate solution under cooling and then extracted with ethyl acetate. The extract was washed with water, dried and then concentrated to dryness. The residue thus obtained was recrystallized from a mixture of ethyl acetate and n-hexane. 2.85 g of N-methyl-N-(4-methoxycarbonylbutyryl)-tryptamine (i.e., 3-[2-(N-methyl-4-methoxycarbonylbutanamido)ethyl]-indole) were thereby obtained. M.p. 101°–102° C. Yield: 95%

EXAMPLE 13

5 g of N-ethyl-N-(4-methoxycarbonylbutyryl)-tryptamine (i.e., 3-[2-(N-ethyl-4-methoxycarbonylbutanamido)ethyl]-indole) were dissolved in 50 ml of acetonitrile, and 5 ml of phosphorus oxychloride were added thereto. The mixture was refluxed for one hour. After the reaction was completed, the mixture was evaporated to remove solvent, whereby 3,4-dihydro-1-(3-methoxycarbonylpropyl)-2-ethyl-β-carbolinium was obtained as a crude product. The crude product thus obtained was dissolved in 100 ml of a mixture of methanol and water (9:1), and sodium borohydride was added thereto under cooling with ice-water until the solution became alkaline. Then, 500 ml of water were added to the aqueous mixture, and the aqueous mixture was extracted with ethyl acetate. The extract was washed with water, dried and evaporated to remove solvent. The oily residue (5 g) thus obtained was purified by silica gel chromatography (Solvent: chloroform-methanol (20:1)), whereby 3.79 g of 1,2,3,4-tetrahydro-1-(3-methoxycarbonylpropyl)-2-ethyl-β-carboline were obtained as a yellow oil. Yield: 80%

IR$\nu_{max}^{film}$ (cm$^{-1}$): 3400, 1730, 1620, 750

Mass (m/e): 300 (M$^+$)

NMR (δ, CDCl$_3$): 3.68 (s, 3H, COOCH$_3$)

Rf-value: 0.27 (silica gel, chloroform-methanol (20:1))

Picrate:

M.p. 141°–142° C. (recrystallized from a mixture of ethyl acetate and n-hexane)

EXAMPLE 14

15.6 g of N-methyl-N-(4-methoxycarbonylbutyryl)-tryptamine (i.e., 3-[2-(N-methyl-4-methoxycarbonylbutanamido)-ethyl]-indole) were treated in the same manner as described in Example 13. 7.9 g of 1,2,3,4-tetrahydro-1-(3-methoxycarbonylpropyl)-2-methyl-β-carboline were thereby obtained. Yield: 53.5%

IR$\nu_{max}^{film}$ (cm$^{-1}$): 3400, 1723

Mass (m/e): 286 (M$^+$)

NMR (δ, CDCl$_3$): 8.4–7.9 (broad, 1H, >NH); 3.66 (s, 3H, COOCH$_3$) 2.40 (s, 3H, >NCH$_3$)

Rf-value: 0.57 (silica gel, chloroform-methanol (20:1))

EXAMPLE 15

10 g of N-isobutyl-N-(4-methoxycarbonylbutyryl)-tryptamine (i.e., 3-[2-(N-isobutyl-4-methoxycarbonylbutanamido)-ethyl]-indole) were treated in the same manner as described in Example 13. 6.75 g of 1,2,3,4-tetrahydro-1-(3-methoxycarbonylpropyl)-2-isobutyl-β-carboline were thereby obtained. Yield: 68.6%

IR$\nu_{max}^{film}$ (cm$^{-1}$): 3420, 1740, 1720, 740

Mass (m/e): 328 (M$^+$)

NMR (δ, CDCl$_3$): 7.89 (broad, 1H, >NH); 7.8–6.9 (m, 4H, aromatic); 3.64 (s, 3H, COOCH$_3$); 0.92, 0.86 (d, d, 6H, —CH(CH$_3$)$_2$)

Rf-value: 0.75 (silica gel, chloroform-methanol (20:1)) pierate:

M.p. 133°–134° C. (recrystallized from a mixture of ethyl acetate and isopropyl ether)

EXAMPLE 16

14.7 g of N-pentyl-N-(4-methoxycarbonylbutyryl)-tryptamine (i.e., 3-[2-(N-pentyl-4-methoxycarbonylbutanamido)-ethyl]-indole) were treated in the same manner as described in Example 13. 6.9 g of 1,2,3,4-tetrahydro-1-(3-methoxycarbonylpropyl)-2-pentyl-β-carboline were thereby obtained. Yield: 49.1%

IR$\nu_{max}^{film}$ (cm$^{-1}$): 3400, 1730

Mass (m/e): 342 (M$^+$)

NMR (δ, CDCl$_3$): 8.42 (broad, 1H, >NH); 7.6–6.9 (m, 4H, aromatic); 3.66 (s, 3H, COOCH$_3$)

Rf-value: 0.16 (silica gel, chloroform-methanol (20:1))

EXAMPLE 17

9.33 g of N-cyclopropylmethyl-N-(4-methoxycarbonylbutyryl)-tryptamine (i.e., 3-[2-(N-cyclopropylmethyl-4-methoxycarbonylbutanamido)ethyl]-indole) were treated in the same manner as described in Example 13. 6.9 g of 1,2,3,4-tetrahydro-1-(3-methoxycarbonylpropyl)-2-cyclopropylmethyl-β-carboline were thereby obtained. Yield: 78.0%

IR$\nu_{max}^{film}$ (cm$^{-1}$): 3400, 1735, 1720, 740

Mass (m/e): 326 (M$^+$)

NMR (δ, CDCl$_3$): 8.10 (broad, 1H, >NH); 7.6–6.8 (m, 4H, aromatic); 3.67 (s, 3H, COOCH$_3$); 1.2–0.0 (m, 5H,)

Rf-value: 0.65 (silica gel, 7% methanol-chloroform)

Picrate:

M.p. 141°–142° C. (recrystallized from a mixture of ethyl acetate and isopropyl ether)

EXAMPLE 18

15.0 g of N-cyclohexylmethyl-N-(4-methoxycarbonylbutyryl)-tryptamine (i.e., 3-[2-(N-cyclohexylmethyl-4-methoxycarbonylbutanamido)ethyl]-indole) were treated in the same manner as described in Example 13. 13.0 g of 1,2,3,4-tetrahydro-1-(3-methoxycarbonylpropyl)-2-cyclohexylmethyl-β-carboline were thereby obtained. Yield: 90.4%

IR$\nu_{max}^{film}$ (cm$^{-1}$): 3400, 1740, 1720, 725

Mass (m/e): 368 (M$^+$)

NMR (δ, CDCl$_3$): 8.0 (broad, 1H, >NH); 8.7–7.0 (m, 4H, aromatic); 3.65 (s, 3H, COOCH$_3$)

Rf-value: 0.63 (silica gel, chloroform-methanol (20:1))

EXAMPLE 19

42.0 g of N-benzyl-N-(4-methoxycarbonylbutyryl)-tryptamine (i.e., 3-[2-(N-benzyl-4-methoxycarbonylbutanamido)-ethyl]-indole) were treated in the same manner as described in Example 13. 23.7 g of 1,2,3,4-tetrahydro-1-(3-methoxycarbonylpropyl)-2-benzyl-β-carboline were thereby obtained. Yield: 59.0%

IR$\nu_{max}^{film}$ (cm$^{-1}$): 3400, 1720, 1615, 1600, 740

Mass (m/e): 362 (M$^+$)

NMR (δ, CDCl$_3$): 7.90 (broad, 1H, >NH); 7.67–7.0 (m, 9H, aromatic); 3.74 (s, 2H, >NCH$_2$—ph); 3.63 (s, 3H, COOCH$_3$)

Rf-value: 0.75 (silica gel, chloroform-methanol (50:1))

Picrate:

M.p. 169°–170° C. (recrystallized from a mixture of ethyl acetate and n-hexane)

EXAMPLE 20

5.85 g of 4-methoxycarbonyl-butanal, 30 ml of ethanol and 3 ml of 35% ethanolic hydrogen chloride were added to 5.65 g of N-ethyltryptamine (i.e., 3-(2-ethylaminoethyl)-indole). The mixture was refluxed for 17 hours. After the reaction was completed, the mixture was evaporated under reduced pressure to remove solvent. Dilute hydrochloric acid was added to the residue under cooling, and the mixture was extracted with ether. The aqueous layer was alkalified with an aqueous 10% sodium hydroxide solution, and extracted with ethyl acetate. The extract was washed with water, dried and evaporated to remove solvent. The oily residue (10 g) thus obtained was purified by silica gel chromatography (Solvent: chloroform-methanol (20:1)), whereby 6.3 g of 1,2,3,4-tetrahydro-1-(3-methoxycarbonylpropyl)-2-ethyl-β-carboline were obtained. Yield: 70%

The physico-chemical properties of this product were identical with those of the product obtained in Example 13.

EXAMPLE 21

(1) 5.65 g of N-ethyl-tryptamine (i.e., 3-(2-ethylaminoethyl)-indole) were dissolved in 30 ml of ethanol, and 9.7 g of 4,4-bis(ethoxycarbonyl)butanal and 3 ml of 35% ethanolic hydrogen chloride were added thereto. The mixture was refluxed for 17 hours. After the reaction was completed, the mixture was evaporated under reduced pressure to remove solvent. Dilute hydrochloric acid was added to the residue thus obtained, and the aqueous mixture was extracted with ethyl acetate. The aqueous layer was alkalified with an aqueous 10% sodium hydroxide solution, and extracted with ethyl acetate. Then, the extract was washed with water, dried and evaporated to remove solvent. The oily residue (10 g) thus obtained was purified by silica gel chromatography (Solvent: chloroform-methanol (50:1)), whereby 5.0 g of 1,2,3,4-tetrahydro-1-[3,3-bis(ethoxycarbonyl)propyl]-2-ethyl-β-carboline were obtained. Yield: 43.0%

IR$\nu_{max}^{film}$ (cm$^{-1}$): 3400, 1750–1715, 1620
Mass (m/e): 386 (M+)
NMR (δ, CDCl$_3$): 8.02 (s, 1H, >NH); 1.40–1.04 (t, 9H, >N—CH$_2$CH$_3$, (COOCH$_2$CH$_3$)$_2$)
Rf-value: 0.55 (silica gel, 7% methanol in chloroform)

(2) 3.0 ml of acetic acid and 1.5 ml of conc. hydrochloric acid were added to 0.70 g of 1,2,3,4-tetrahydro-1-[3,3-bis(ethoxycarbonyl)propyl]-2-ethyl-β-carboline. The mixture was stirred at 120° C. for 5 hours. After the reaction was completed, the mixture was evaporated to remove solvent, whereby 1,2,3,4-tetrahydro-1-(3-carboxypropyl)-2-ethyl-β-carboline was obtained as a crude product. 30 ml of 10% methanolic hydrogen chloride were added to the crude product, and the mixture was refluxed for 2 hours. After the reaction was completed, the mixture was concentrated. The residue thus obtained was alkalified with an aqueous saturated sodium bicarbonate solution under cooling, and extracted with ethyl acetate. The extract was washed with water, dried and evaporated to remove solvent. The residue thus obtained was purified by silica gel chromatography (Solvent: chloroform-methanol (20:1)), whereby 470 mg of 1,2,3,4-tetrahydro-1-(3-methoxycarbonylpropyl)-2-ethyl-β-carboline were obtained. Yield: 84.0%

The physico-chemical properties of this product were identical with those of the product obtained in Example 13.

EXAMPLE 22

2 ml of methanol, 2 ml of conc. hydrochloric acid and 10 ml of 10% hydrochloric acid were added to 0.7 g of 1,2,3,4-tetrahydro-1-[3,3-bis(ethoxycarbonyl)propyl]-2-ethyl-β-carboline, and the mixture was stirred at 120° C. for 7 hours. After the reaction was completed, the mixture was evaporated under reduced pressure to remove solvent. The residue thus obtained was recrystallized from a mixture of ethanol and ether. 0.49 g of 1,2,3,4-tetrahydro-1-(3-carboxypropyl)-2-ethyl-β-carboline hydrochloride was obtained. M.p. 194°–197° C. (decomp.) Yield: 73.5%

IR$\nu_{max}^{Nujol}$ (cm$^{-1}$): 3300, 2700–2400, 1720
Mass (m/e): 286 (M+)

EXAMPLE 23

(1) 1.78 g of N-methyl-tryptamine (i.e., 3-(2-methylaminoethyl)-indole) and 3.1 g of 4,4-bis(ethoxycarbonyl)-butanal were treated in the same manner as described in Example 21-(1). 2.1 g of 1,2,3,4-tetrahydro-1-[3,3-bis-(ethoxycarbonyl)propyl]-2-methyl-β-carboline were thereby obtained. Yield: 55.0%

IR$\nu_{max}^{film}$ (cm$^{-1}$): 3400, 1750–1715, 1620
Mass (m/e): 372 (M+)
NMR (δ, CDCl$_3$): 8.0 (broad, 1H, >NH); 2.4 (s, 3H, N—CH$_3$)
Rf-value: 0.6 (silica gel, 7% methanol in chloroform)

(2) 25 ml of 5% hydrochloric acid were added to 1.08 g of 1,2,3,4-tetrahydro-1-[3,3-bis(ethoxycarbonyl)-propyl]-2-methyl-β-carboline, and the mixture was stirred at 80° C. for 5 hours. After the reaction was completed, the mixture was treated with activated charcoal powder and then condensed under reduced pressure. 930 mg of 1,2,3,4-tetrahydro-1-(3-carboxypropyl)-2-methyl-β-carboline hydrochloride were thereby obtained. Yield: 79.8%

M.p. 139°–143° C. (recrystallized from a mixture of ethanol and ether)
IR$\nu_{max}^{Nujol}$ (cm$^{-1}$): 3300, 2700–2400, 1720
Mass (m/e): 272 (M+)

EXAMPLE 24

10 ml of methanol and 3 ml of 10% methanolic hydrogen chloride were added to 2.86 g of 1,2,3,4-tetrahydro-1-(3-carboxypropyl)-2-ethyl-β-carboline, and the mixture was refluxed for 2 hours. After the reaction was completed, the mixture was concentrated to one third volume. The concentrated mixture was alkalified with an aqueous saturated sodium bicarbonate solution, and then extracted with benzene. The extract was washed with water, dried and evaporated to remove solvent. 2.70 g of 1,2,3,4-tetrahydro-1-(3-methoxycarbonylpropyl)-2-ethyl-β-carboline were obtained. Yield: 90%

The physico-chemical properties of this product were identical with those of the product obtained in Example 13.

EXAMPLE 25

15 ml of ethanol and 3 ml of 10% ethanolic hydrogen chloride were added to 2.86 g of 1,2,3,4-tetrahydro-1-(3-carboxypropyl)-2-ethyl-β-carboline, and the mixture was refluxed for 2 hours. After the reaction was completed, the mixture was evaporated under reduced pressure to remove solvent. The residue thus obtained was alkalified with an aqueous saturated sodium bicarbonate solution and then extracted with ethyl acetate. The extract was washed with water, dried and evaporated to remove solvent. 2.67 g of 1,2,3,4-tetrahydro-1-(3-ethoxycarbonylpropyl)-2-ethyl-β-carboline were obtained. Yield: 85.0%.

IR$\nu_{max}^{film}$ (cm$^{-1}$): 3400, 1740, 1720, 1620
Mass (m/e): 314 (M+)
Rf-value: 0.40 (silica gel, chloroform-methanol (20:1))

EXAMPLE 26

5 g of N-ethyl-tryptamine (i.e., 3-(2-ethylaminoethyl)-indole) were dissolved in 100 ml of absolute benzene, and a solution of 4.70 g of α-keto-adipic acid in 50 ml of absolute dioxane was added thereto at room temperature. The mixture was refluxed for 20 hours. After the reaction was completed, the mixture was evaporated to remove solvent. The residue thus obtained was recrystallized from ethanol, whereby 3.51 g of 1,2,3,4-tetrahydro-1-carboxy-1-(3-carboxypropyl)-2-ethyl-β-carboline were obtained. Yield: 38.0%

M.p. 213°–217° C. (decomp.)
IR$\nu_{max}^{Nujol}$ (cm$^{-1}$): 3325, 1715, 1690, 1580
Mass (m/e): 286 (M$^+$—CO$_2$)

On the other hand, the mother liquor which was obtained after isolation of the above-mentioned β-carboline compound was concentrated to dryness. 4.57 g of 1,2,3,4-tetrahydro-1-(3-carboxypropyl)-2-ethyl-β-carboline were thereby obtained. Yield: 60%
Hydrochloride:
M.p. 194°–197° C. (decomp.) (recrystallized from a mixture of ethanol and ether)

EXAMPLE 27

15 ml of ethyl iodide were added to 1.80 g of 3,4-dihydro-1-(3-methoxycarbonylpropyl)-β-carboline [cf. Rec. Trav. Chim., Vol. 84, No. 9–10, pp 1183–1199(1965)], and the mixture was stirred at 70°–80° C. overnight. After the reaction was completed, the mixture was concentrated to dryness, whereby 3,4-dihydro-1-(3-methoxycarbonylpropyl)-2-ethyl-β-carbolinium iodide was obtained as a crude product. The crude product was dissolved in 20 ml of ethanol, and one g of sodium borohydride was added thereto. The mixture was stirred at room temperature for one hour. Then, the mixture was extracted with ethyl acetate. The extract was washed with water, dried and evaporated to remove solvent. The residue thus obtained was purified by silica gel chromatography (Solvent: 5% methanol-chloroform), whereby 0.2 g of 1,2,3,4-tetrahydro-1-(3-methoxycarbonylpropyl)-2-ethyl-β-carboline was obtained. Yield: 11%

The physico-chemical properties of this product were identical with those of the product obtained in Example 13.

EXAMPLE 28

60 ml of absolute benzene were added to 3.11 g of hexamethyldisilazane sodium salt (i.e., [(CH$_3$)$_3$Si]$_2$N-.Na), and a solution of 2.55 g of 1,2,3,4-tetrahydro-1-(3-methoxycarbonylpropyl)-2-ethyl-β-carboline in 30 ml of absolute benzene was added dropwise thereto in nitrogen gas atmosphere under cooling with ice-water. The mixture was stirred at room temperature for one hour. After the reaction was completed, an aqueous saturated sodium bicarbonate solution was added to the mixture under cooling. Then, the mixture was extracted with benzene. The extract was washed with water, dried and evaporated to remove solvent. The oily residue (1.85 g) thus obtained was purified by silica gel chromatography (Solvent: chloroform-methanol (50:1)), whereby 950 mg of 1,2,3,3a,4,5,6,7-octahydro-3-ethyl-7-oxo-azepino[1,2,3-lm]-β-carboline were obtained. Yield: 42.0%

M.p. 67.5°–69.5° C. (recrystallized from n-hexane)
Mass (m/e): 268 (M$^+$)
Hydrochloride:
M.p. 247°–249° C. (recrystallized from methanol)
IR$\nu_{max}^{Nujol}$ (cm$^{-1}$): 2600–2460, 1695
NMR (δ, DMSO): 8.30–8.10 (m, 1H, aromatic); 7.70–7.10 (m, 3H, aromatic); 1.40 (t, 3H, —CH$_2$CH$_3$)

EXAMPLE 29

3.14 g of 1,2,3,4-tetrahydro-1-(3-ethoxycarbonylpropyl)-2-ethyl-β-carboline were treated in the same manner as described in Example 28. 1.61 g of 1,2,3,3a,4,5,6,7-octahydro-3-ethyl-7-oxo-azepino[1,2,3-lm]-β-carboline were obtained. Yield: 60%

The physico-chemical properties of this product were identical with those of the product obtained in Example 28.

EXAMPLE 30

4.0 g of 1,2,3,4-tetrahydro-1-(3-methoxycarbonylpropyl)-2-methyl-β-carboline were treated in the same manner as described in Example 28. 1.80 g of 1,2,3,3a,4,5,6,7-octahydro-3-methyl-7-oxo-azepino[1,2,3-lm]-β-carboline were thereby obtained. Yield: 47.6%

M.p. 94°–95° C. (recrystallized from n-hexane)
IR$\nu_{max}^{Nujol}$ (cm$^{-1}$): 1693
Mass (m/e): 254 (M$^+$)
NMR (δ, CDCl$_3$): 8.6–8.3 (m, 1H, aromatic); 7.7–7.07 (m, 3H, aromatic); 3.9–3.5 (m, 1H,

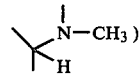

2.50 (s, 3H, >NCH$_3$)
Hydrochloride:
M.p. 271°–273° C. (recrystallized from methanol)
IR$\nu_{max}^{Nujol}$ (cm$^{-1}$): 2700–2300, 1698
NMR (δ, D$_2$O): 8.3–8.05 (m, 1H, aromatic) 7.64–7.30 (m, 3H, aromatic) 3.08 (s, 3H, >NCH$_3$)

EXAMPLE 31

5.5 g of 1,2,3,4-tetrahydro-1-(3-methoxycarbonylpropyl)-2-isobutyl-β-carboline were treated in the same manner as described in Example 28. 2.56 g of 1,2,3,3a,4,5,6,7-octahydro-3-isobutyl-7-oxo-azepino[1,2,3-lm]-β-carboline were thereby obtained as an oil. Yield: 51.8%

Mass (m/e): 296 (M$^+$)
NMR (δ, CDCl$_3$): 8.46 (m, 1H, aromatic); 7.6–7.2 (m, 3H, aromatic); 3.80 (m, broad, 1H,

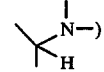

0.89, 0.99 (d, d, 6H, —CH(CH$_3$)$_2$)
Hydrochloride:
M.p. 227°–228° C. (recrystallized from a mixture of ethanol and isopropyl ether)
IR$\nu_{max}^{Nujol}$ (cm$^{-1}$): 2700–2100, 1695

EXAMPLE 32

6.60 g of 1,2,3,4-tetrahydro-1-(3-methoxycarbonylpropyl)-2-pentyl-β-carboline were treated in the same manner as described in Example 28. 2.95 g of 1,2,3,3a,4,5,6,7-octahydro-3-pentyl-7-oxo-azepino[1,2,3-lm]-β-carboline were thereby obtained as an oil. Yield: 50.0%

IR$\nu_{max}^{film}$ (cm$^{-1}$): 1695
Mass (m/e): 310 (M$^+$)

NMR (δ, CDCl₃): 8.49–8.26 (m, 1H, aromatic) 8.50–7.00 (m, 3H, aromatic)
Hydrochloride:
M.p. 218°–220° C. (recrystallized from a mixture of methanol and isopropyl ether)
IR$ν_{max}^{Nujol}$ (cm⁻¹): 2700–2300, 1695
NMR (δ, D₂O): 8.33–7.94 (m, 1H, aromatic); 7.72–7.19 (m, 3H, aromatic)

EXAMPLE 33

6.0 g of 1,2,3,4-tetrahydro-1-(3-methoxycarbonylpropyl)-2-cyclopropylmethyl-β-carboline were treated in the same manner as described in Example 28. 3.25 g of 1,2,3,3a,4,5,6,7-octahydro-3-cyclopropylmethyl-7-oxo-azepino[1,2,3-lm]-β-carboline were thereby obtained as an oil. Yield: 60.2%

Mass (m/e): 294 (M⁺)

NMR (δ, CDCl₃): 8.39 (m, 1H, aromatic); 7.6–7.2 (m, 3H, aromatic); 4.10 (broad, m, 1H,

1.2–0.05 (m, 5H,    )
Hydrochloride:
M.p. 242°–243° C. (recrystallized from ethanol)
IR$ν_{max}^{Nujol}$ (cm⁻¹): 2700–2200, 1705

EXAMPLE 34

12.0 g of 1,2,3,4-tetrahydro-1-(3-methoxycarbonylpropyl)-2-cyclohexylmethyl-β-carboline were treated in the same manner as described in Example 28. 6.2 g of 1,2,3,3a,4,5,6,7-octahydro-3-cyclohexylmethyl-7-oxo-azepino[1,2,3-lm]-β-carboline were thereby obtained as colorless prisms. Yield: 56.0%

M.p. 94°–95.5° C. (recrystallized from ethanol)
IR$ν_{max}^{Nujol}$ (cm⁻¹): 1695
Mass (m/e): 336 (M⁺)
NMR (δ, CDCl₃): 8.46 (m, 1H, aromatic) 7.43–7.16 (m, 3H, aromatic) 4.16–3.50 (m, 1H,

3.50–0.33 (m, 23H)
Hydrochloride:
M.p. 200°–203° C. (recrystallized from a mixture of ethanol and ethyl acetate)
IR$ν_{max}^{Nujol}$ (cm⁻¹): 2700–2300, 1690
NMR (δ, D₂O): 8.16 (m, 1H, aromatic); 7.66–7.3 (m, 3H, aromatic); 3.84 (m, 1H,

EXAMPLE 35

23.3 g of 1,2,3,4-tetrahydro-1-(3-methoxycarbonylpropyl)-2-benzyl-β-carboline were treated in the same manner as described in Example 28. 14.27 g of 1,2,3,3a,4,5,6,7-octahydro-3-benzyl-7-oxo-azepino[1,2,3-lm]-β-carboline were thereby obtained. Yield: 68%

M.p. 110°–111° C. (recrystallized from isopropyl ether)
IR$ν_{max}^{Nujol}$ (cm⁻¹): 1690
Mass (m/e): 330 (M⁺)
NMR (δ, CDCl₃): 8.68–8.21 (m, 1H, aromatic) 7.66–7.0 (m, 8H, aromatic) 3.73 (s, 2H, NCH₂—ph) 4.11–3.66 (m, 1H,

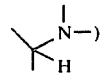

Hydrochloride:
M.p. 255°–256° C. (recrystallized from methanol)
IR$ν_{max}^{Nujol}$ (cm⁻¹): 2380–2330, 1700

EXAMPLE 36

10 g of polyphosphoric acid were added to one g of 1,2,3,4-tetrahydro-1-(3-methoxycarbonylpropyl)-2-methyl-β-carboline, and the mixture was stirred at 140° C. for 10 minutes. After the reaction was completed, water was added to the mixture under cooling, and the aqueous mixture was made alkaline with dilute sodium hydroxide. Then, said mixture was extracted with ethyl acetate. The extract was washed with water, dried and evaporated to remove solvent. The residue thus obtained was purified by silica gel chromatography (Solvent: chloroform-methanol(20:1)), whereby 530 mg of 1,2,3,3a,4,5,6,7-octahydro-3-methyl-7-oxo-azepino[1,2,3-lm]-β-carboline were obtained. Yield: 60%

M.p. 94°–95° C. (recrystallized from n-hexane)
Hydrochloride:
M.p. 271°–273° C. (recrystallized from methanol)

EXAMPLE 37

6.5 g of 1,8-diazabicyclo[5,4,0]undecene-7 and 40 ml of anhydrous toluene were added to 14.0 g of 1,2,3,4-tetrahydro-1-(3-methoxycarbonylpropyl)-2-cyclohexylmethyl-β-carboline. The mixture was refluxed in nitrogen atmosphere for 39 hours. After the reaction was completed, the reaction mixture was evaporated under reduced pressure to remove solvent. The residue thus obtained was purified by silica gel chromatography (Solvent: 1% methanol-chloroform), and then recrystallized from ethanol, whereby 7.8 g of 1,2,3,3a,4,5,6,7-octahydro-3-cyclohexylmethyl-7-oxo-azepino[1,2,3-lm]-β-carboline were obtained as colorless prisms. Yield: 61.4%

The physico-chemical properties of this product were identical with those of the product obtained in Example 34.

EXAMPLE 38

10 ml of anhydrous toluene and 310 mg of 1,8-diazabicyclo[5,4,0]undecene-7 were added to 730 mg of 1,2,3,4-tetrahydro-1-(3-methoxycarbonylpropyl)-2-benzyl-β-carboline, and the mixture was refluxed for 6 days. After the reaction was completed, ethyl acetate was added to the reaction mixture, and said mixture was washed with an aqueous saturated sodium chloride solution, dried, and then condensed to dryness. The residue thus obtained was purified by silica gel chromatography (Solvent: 5% ethyl acetate-chloroform), and then recrystallized from a mixture of methanol and isopropyl ether, whereby 550 mg of 1,2,3,3a,4,5,6,7-octahydro-3-benzyl-7-oxo-azepino-[1,2,3-lm]-β-carboline were obtained as colorless prisms. Yield: 83%

The physico-chemical properties of this product were identical with those of the product obtained in Example 35.

EXAMPLE 39

10 ml of anhydrous toluene and 248 mg of 1,5-diazabicyclo[4,3,0]nonene-5 were added to 730 mg of 1,2,3,4-tetrahydro-1-(3-methoxycarbonylpropyl)-2-benzyl-β-carboline, and the mixture was refluxed for 2 days. After the reaction was completed, the reaction mixture was treated in the same manner as described in Example 38, whereby 463 mg of 1,2,3,3a,4,5,6,7-octahydro-3-benzyl-7-oxo-azepino[1,2,3-lm]-β-carboline were obtained. Yield: 70.0%

The physico-chemical properties of this product were identical with those of the product obtained in Example 35.

EXAMPLE 40

860 mg of sodium were added to 18 ml of tertiary amylalcohol-absolute toluene (1:1), and the mixture was refluxed for 5 hours. Then, the reaction mixture was condensed to dryness, whereby sodium tertiary amyloxide was obtained. 20 ml of absolute toluene and 1.09 g of 1,2,3,4-tetrahydro-1-(3-methoxycarbonylpropyl)-2-benzyl-β-carboline were added to said sodium tertiary amyloxide under ice-cooling, and the mixture was stirred at the same temperature for 3 hours. After the reaction was completed, ethyl acetate was added to the reaction mixture. Said mixture was washed with an aqueous saturated sodium chloride solution, dried and then condensed. The residue thus obtained was purified by silica gel chromatography (Solvent: chloroform), and then recrystallized from a mixture of methanol and isopropyl ether, whereby 300 mg of 1,2,3,3a,4,5,6,7-octahydro-3-benzyl-7-oxo-azepino[1,2,3-lm]-β-carboline were obtained. Yield: 30.3%

The physico-chemical properties of this product were identical with those of the product obtained in Example 35.

EXAMPLE 41

10 g of polyphosphoric acid were added to one g of 1,2,3,4-tetrahydro-1-(3-carboxypropyl)-2-methyl-β-carboline hydrochloride, and the mixture was stirred at 140° C. for 10 minutes. After the reaction was completed, ice-water was added to the mixture, and the aqueous mixture was basified with dilute sodium hydroxide. Then said mixture was extracted with ethyl acetate. The extract was washed with water, dried and evaporated to remove solvent. The residue thus obtained was purified by silica gel chromatography (Solvent: chloroform-methanol(20:1), whereby 538 mg of 1,2,3,3a,4,5,6,7-octahydro-3-methyl-7-oxo-azepino[1,2,3-lm]-β-carboline were thereby obtained. Yield: 68.0%

The physico-chemical properties of this product were identical with those of the product obtained in Example 30.

EXAMPLE 42

10 g of polyphosphoric acid were added to one g of N-methyl-N-(4-methoxycarbonylbutyryl)-tryptamine (i.e., 3-[2-(N-methyl-4-methoxycarbonylbutanamido)ethyl]-indole), and the mixture was stirred at 130° C. for 20 minutes. Ice-water was added to the mixture, and it was neutralized with dilute sodium hydroxide. One g of sodium borohydride was added to the mixture, and said mixture was further stirred at room temperature for one hour. After the reaction was completed, the mixture was extracted with ethyl acetate. The extract was washed with water, dried and evaporated to remove solvent. The residue thus obtained was purified by silica gel chromatography (Solvent: chloroform-methanol(20:1)), whereby 585 mg of 1,2,3,3a,4,5,6,7-octahydro-3-methyl-7-oxo-azepino[1,2,3-lm]-β-carboline were obtained. Yield: 65.8%

The physico-chemical properties of this product were identical with those of the product obtained in Example 30.

EXAMPLE 43

10 g of polyphosphoric acid were added to one g of N-methyl-N-(4-carboxybutyryl)-tryptamine (i.e., 3-[2-(N-methyl-4-carboxybutanamido)ethyl]-indole), and the mixture was stirred at 130° C. for 20 minutes. Ice-water was added to the mixture, and it was neutralized with dilute sodium hydroxide. One g of sodium borohydride was added to the mixture, and said mixture was further stirred for one hour. After the reaction was completed, the mixture was extracted with ethyl acetate. The extract was washed with water, dried and evaporated to remove solvent. The residue thus obtained was purified by silica gel chromatography (Solvent: chloroform-methanol (20:1)), whereby 497 mg of 1,2,3,3a,4,5,6,7-octahydro-3-methyl-7-oxo-azepino[1,2,3-lm]-β-carboline were obtained. Yield: 56%

The physico-chemical properties of this product were identical with those of the product obtained in Example 30.

EXAMPLE 44

3.3 g of N-isobutyl-N-(4-carboxybutyryl)-tryptamine (i.e., 3-[2-(N-idobutyl-4-carboxybutanamido)ethyl]-indole) were treated in the same manner as described in Example 43. 1.84 g of 1,2,3,3a,4,5,6,7-octahydro-3-isobutyl-7-oxo-azepino[1,2,3-lm]-β-carboline were thereby obtained. Yield: 62%

The physico-chemical properties of this product were identical with those of the product obtained in Example 31.

EXAMPLE 45

400 ml of aqueous 50% methanol, 5 ml of conc. hydrochloric acid and one g of 10% palladium-carbon were added to 8.90 g of 1,2,3,3a,4,5,6,7-octahydro-3-benzyl-7-oxo-azepino[1,2,3-lm]-β-carboline. The mixture was shaken at room temperature for 3 hours in hydrogen atmosphere under atmospheric pressure. After hydrogen uptake was completed, insoluble materials were removed by filtration. The filtrate was evaporated under reduced pressure to remove solvent. The residue thus obtained was recrystallized from methanol, whereby 5.3 g of 1,2,3,3a,4,5,6,7-octahydro-7-oxo-azepino[1,2,3-lm]-β-carboline hydrochloride were obtained as needles. M.p. 274°–277° C. (decomp.) Yield: 71.0%

IR$\nu_{max}^{Nujol}$ (cm$^{-1}$): 2800–2450, 1700, 1615, 755

Free base:

M.p. 110°–112.5° C. (recrystallized from isopropyl ether)

IR$\nu_{max}^{Nujol}$ (cm$^{-1}$): 3280, 1690, 1600, 750

Mass (m/e): 240 (M+)
NMR (δ, CDCl₃): 8.66–8.29 (m, 1H, aromatic); 7.56–7.00 (m, 3H, aromatic); 4.50–2.63 (m, 7H); 2.40–1.16 (m, 4H); 1.55 (s, 1H, >NH)

EXAMPLE 46

10 g of polyphosphoric acid were added to one g of 1,2,3,4-tetrahydro-1-carboxy-1-(3-carboxypropyl)-2-ethyl-β-carboline, and the mixture was stirred at 130° C. for 20 minutes. After the reaction was completed, ice-water was added to the mixture, and the aqueous mixture was made alkaline with dilute sodium hydroxide. Then, said mixture was extracted with ethyl acetate. The extract was washed with water, dried and evaporated to remove solvent. The residue thus obtained was purified by silica gel chromatography (Solvent: chloroform-methanol (20:1)), whereby 597 mg of 1,2,3,3a,4,5,6,7-octahydro-3-ethyl-7-oxo-azepino[1,2,3-lm]-β-carboline were obtained. Yield: 70%

The physico-chemical properties of this product were identical with those of the product obtained in Example 28.

EXAMPLE 47

30 ml of dimethylformamide, 1.28 g of n-propyl iodide and 1.11 g of potassium carbonate were added to 1.21 g of 1,2,3,3a,4,5,6,7-octahydro-7-oxo-azepino[1,2,3-lm]-β-carboline, and the mixture was stirred at room temperature for 17 hours. After the reaction was completed, the reaction mixture was poured into ice-water, and the aqueous mixture was extracted with ethyl acetate. The extract was washed with water, dried and then evaporated under reduced pressure to remove solvent. The residue thus obtained was purified by silica gel chromatography (Solvent: 2% methanol-chloroform), whereby 1.04 g of 1,2,3,3a,4,5,6,7-octahydro-3-n-propyl-7-oxo-azepino[1,2,3-lm]-β-carboline were obtained as an oil. Yield: 87.8%

IRν$_{max}^{film}$ (cm⁻¹): 1695, 1620, 760
Mass (m/e): 282 (M+)
NMR (δ, CDCl₃): 8.67–8.27 (m, 3H, aromatic); 7.67–7.07 (m, 3H, aromatic); 4.23–3.57 (m, 1H,

3.50–1.17 (m, 14H); 0.92 (t, J=6.7 Hz, 3H, —CH₂CH₂CH₃)
Rf-value: 0.65 (Silica gel, 5% methanol-chloroform)
Hydrochloride:
M.p. 239.5°–241° C. (decomp.) (needles) (recrystallized from a mixture of isopropylalcohol and isopropyl ether)
IRν$_{max}^{Nujol}$ (cm⁻¹): 2460, 1705, 1620, 755

EXAMPLE 48

20 ml of acetonitrile and 830 mg of potassium carbonate were added to 1.20 g of 1,2,3,3a,4,5,6,7-octahydro-7-oxoazepino[1,2,3-lm]-β-carboline, and the mixture was stirred at room temperature for 10 minutes. 1.20 g of isopropyl iodide were added to the mixture, and said mixture was refluxed for 40 hours. After the reaction was completed, the reaction mixture was evaporated to remove solvent. The residue was dissolved in ethyl acetate, and the solution was washed with water, dried and then evaporated under reduced pressure to remove solvent. The residue thus obtained was purified by silica gel chromatography. (Solvent: 1% methanol-chloroform), whereby 1.30 g of 1,2,3,3a,4,5,6,7-octahydro-3-isopropyl-7-oxo-azepino[1,2,3-lm]-β-carboline was obtained as an oil. Yield: 92.2%

IRν$_{max}^{film}$ (cm⁻¹): 1690, 1620, 1455
Mass (m/e): 282 (M+), 212 (base peak)
NMR (δ, CDCl₃): 8.4 (m, 1H, aromatic); 7.6–7.1 (m, 3H, aromatic); 4.1 (broad, m, 1H,

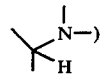

1.14 (d, J=6.2 Hz, 6H, N—CH(CH₃)₂)
Hydrochloride:
M.p. 251°–253° C. (decomp.) (colorless granules) (recrystallized from methanol)
IRν$_{max}^{Nujol}$ (cm⁻¹): 2700–2200, 1690, 1620, 1470, 775

EXAMPLE 49

20 ml of acetonitrile and 830 mg of potassium carbonate were added to 1.20 g of 1,2,3,3a,4,5,6,7-octahydro-7-oxoazepino[1,2,3-lm]-β-carboline, and the mixture was stirred at room temperature for 10 minutes. 825 mg of n-butyl bromide and 100 mg of potassium iodide were added to the mixture, and said mixture was refluxed for 20 hours under stirring. After the reaction was completed, the reaction mixture was evaporated to remove solvent. The residue was dissolved in ethyl acetate, and the solution was washed with water, dried and then evaporated under reduced pressure to remove solvent. The residue thus obtained was purified by silica gel chromatography (Solvent: 1% methanol-chloroform), whereby 1.37 g of 1,2,3,3a,4,5,6,7-octahydro-3-n-butyl-7-oxo-azepino-[1,2,3-lm]-β-carboline were obtained as an oil. Yield: 92.6%

IRν$_{max}^{film}$ (cm⁻¹): 1690, 1615, 1450
Mass (m/e): 296 (M+), 226 (base peak), 183
NMR (δ, CDCl₃): 8.40 (m, 1H, aromatic); 7.6–7.1 (m, 3H, aromatic); 3.9 (m, 1H,

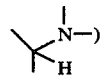

0.93 (t.like, 3H, N—(CH₂)₃—CH₃)
Hydrochloride:
M.p. 242°–244° C. (decomp.) (colorless prisms) (recrystallized from a mixture of ethanol and isopropyl ether)
IRν$_{max}^{Nujol}$ (cm⁻¹): 2600–2200, 1695, 1620, 1470, 1450 765

EXAMPLE 50

10 ml of dimethylformamide were added to 1.20 g of 1,2,3,3a,4,5,6,7-octahydro-7-oxo-azepino[1,2,3-lm]-β-carboline, and 0.90 g of potassium carbonate and 1.33 g of cyclohexylmethyl bromide were added thereto. The mixture was stirred at room temperature for 24 hours. After the reaction was completed, the reaction mixture was poured into ice-water. The aqueous mixture was extracted with ethyl acetate, and the extract was washed with water, dried and then evaporated under reduced pressure to remove solvent. The residue thus obtained was purified by silica gel chromatography (Solvent: 1% methanol-chloroform), whereby 1.19 g of 1,2,3,3a,4,5,6,7-octahydro-3-cyclohexylmethyl-7-oxo-azepino[1,2,3-lm]-β-carboline were obtained as colorless prisms. Yield: 71%

The physico-chemical properties of this product were identical with those of the product obtained in Example 34.

EXAMPLE 51

1.21 g of 1,2,3,3a,4,5,6,7-octahydro-7-oxo-azepino[1,2,3-lm]-β-carboline and 5 g of methyl iodide were treated in the same manner as described in Example 47, whereby 1.16 g of 1,2,3,3a,4,5,6,7-octahydro-3-methyl-7-oxo-azepino[1,2,3-lm]-β-carboline were obtained. Yield: 92%

The physico-chemical properties of this product were identical with the product obtained in Example 30.

EXAMPLE 52

1.21 g of 1,2,3,3a,4,5,6,7-octahydro-7-oxo-azepino[1,2,3,-lm]-β-carboline and 1.2 g of ethyl bromide were treated in the same manner as described in Example 48, whereby 1.15 g of 1,2,3,3a,4,5,6,7-octahydro-3-ethyl-7-oxo-azepino[1,2,3-lm]-β-carboline were obtained. Yield: 86%

The physico-chemical properties of this product were identical with those of the product obtained in Example 28.

EXAMPLE 53

1.21 g of 1,2,3,3a,4,5,6,7-octahydro-7-oxo-azepino[1,2,3-lm]-β-carboline and 0.825 g of isobutyl bromide were treated in the same manner as described in Example 48, whereby 1.15 g of 1,2,3,3a,4,5,6,7-octahydro-3-isobutyl-7-oxo-azepino[1,2,3-lm]-β-carboline were obtained as an oil. Yield: 78%

The physico-chemical properties of this product were identical with those of the product obtained in Example 31.

EXAMPLE 54

1.21 g of 1,2,3,3a,4,5,6,7-octahydro-7-oxo-azepino[1,2,3,-lm]-β-carboline and 1.0 g of n-pentyl bromide were treated in the same manner as described in Example 48, whereby 1.35 L g of 1,2,3,3a,4,5,6,7-octahydro-3-n-pentyl-7-oxoazepino[1,2,3-lm]-β-carboline were obtained as an oil. Yield: 87%

The physico-chemical properties of this product were identical with those of the product obtained in Example 32.

EXAMPLE 55

1.21 g of 1,2,3,3a,4,5,6,7-octahydro-7-oxo-azepino[1,2,3-lm]-β-carboline and 1.0 g of cyclopropylmethyl bromide were treated in the same manner as described in Example 48, whereby 1.16 L g of 1,2,3,3a,4,5,6,7-octahydro-3-cyclopropylmethyl-7-oxo-azepino[1,2,3-lm]-β-carboline were obtained as an oil. Yield: 79%

The physico-chemical properties of this product were identical with those of the product obtained in Example 33.

EXAMPLE 56

1.21 g of 1,2,3,3a,4,5,6,7-octahydro-7-oxo-azepino[1,2,3-lm]-β-carboline and 1.02 g of benzyl bromide were treated in the same manner as described in Example 47, whereby 1.48 g of 1,2,3,3a,4,5,6,7-octahydro-3-benzyl-7-oxo-azepino[1,2,3-lm]-β-carboline were obtained. Yield: 90%

The physico-chemical properties of this product were identical with those of the product obtained in Example 35.

EXAMPLE 57

15 ml of dimethylformamide, 1.2 g of phenethyl bromide and 1.04 g of potassium carbonate were added to 1.30 g of 1,2,3,3a,4,5,6,7-octahydro-7-oxo-azepino[1,2,3-lm]-β-carboline, and the mixture was stirred at room temperature for 24 hours and further stirred at 80° C. for 4 hours. After the reaction was completed, the reaction mixture was poured into ice-water and the aqueous mixture was extracted with ethyl acetate. The extract was washed with water, dried and evaporated under reduced pressure to remove solvent. The residue thus obtained was purified by silica gel chromatography (Solvent: 1% methanol-chloroform), whereby 700 mg of 1,2,3,3a,4,5,6,7-octahydro-3-phenethyl-7-oxo-azepino[1,2,3-lm]-β-carboline were obtained. Yield: 37.8%

M.p. 88°–93.5° C. (recrystallized from n-hexane)
Mass (m/e): 344 (M+)
IR$\nu_{max}^{Nujol}$ (cm$^{-1}$): 1690, 1615, 1605, 750, 700
NMR (δ, CDCl$_3$): 8.66–8.16 (m, 1H); 7.66–7.00 (m, 8H); 4.26–3.56 (m, 1H); 3.43–2.50 (m, 10H); 2.43–1.40 (m, 4H)
Rf-value: 0.53 (Silica gel, 2% methanol-chloroform)
Hydrochloride:
M.p. 213°–214.5° C. (decomp.) (needles) (recrystallized from a mixture of ethanol and isopropyl ether)
IR$\nu_{max}^{Nujol}$ (cm$^{-1}$): 3430 (H$_2$O), 2400, 1690, 1620, 755, 700

EXAMPLE 58

20 ml of dimethylformamide and 1.93 g of potassium carbonate were added to 2.40 g of 1,2,3,3a,4,5,6,7-octahydro-7-oxo-azepino[1,2,3-lm]-β-carboline, and a solution of 2.0 g of bromoacetone in 5 ml of dimethylformamide was added thereto under ice-cooling. The mixture was stirred at room temperature for 3 hours. After the reaction was completed, the reaction mixture was poured into ice-water. The aqueous mixture was extracted with ethyl acetate, and the extract was washed with water, dried and evaporated under reduced pressure to remove solvent. The residue thus obtained was purified by silica gel chromatography (Solvent: 1% methanol-chloroform), whereby 2.47 g of 1,2,3,3a,4,5,6,7-octahydro-3-acetylmethyl-7-oxoazepino[1,2,3-lm]-β-carboline were obtained. Yield: 91%

M.p. 97°–99.5° C. (recrystallized from a mixture of n-hexane and isopropyl ether)
IR$\nu_{max}^{Nujol}$ (cm$^{-1}$): 1715, 1685, 1610, 755
Mass (m/e): 296 (M+)
NMR (δ, CDCl$_3$): 8.60–8.26 (m, 1H, aromatic); 7.66–7.17 (m, 3H, aromatic); 4.17–3.66 (m, 1H,

3.43 (s, 2H, N-CH$_2$—CO—); 2.14 (s, 3H, -COCH$_3$); 3.33–1.50 (m, 10H)
Rf-value: 0.70 (Silica gel, 6% methanol-chloroform)
Hydrochloride:

M.p. 214°–218° C. (decomp.) (colorless needles) (recrystallized from methanol)

IR$\nu_{max}^{Nujol}$ (cm$^{-1}$): 3500 (H$_2$O), 3420, 2770–2300, 1725, 1685, 1610

EXAMPLE 59

8 ml of vinyl methyl ketone and 0.1 ml of acetic acid were added to 2.0 g of 1,2,3,3a,4,5,6,7-octahydro-7-oxoazepino[1,2,3-lm]-β-carboline, and the mixture was stirred at 60° C. for 1.5 hours. After the reaction was completed, the reaction mixture was acidified with 10% hydrochloric acid under ice-cooling, and then washed with ether. The aqueous layer was alkalized with potassium carbonate, and then extracted with ethyl acetate. The extract was washed with water, dried and evaporated under reduced pressure to remove solvent. The residue thus obtained was recrystallized from n-hexane, whereby 2.51 g of 1,2,3,3a,4,5,6,7-octahydro-3-(2-acetylethyl)-7-oxo-azepino[1,2,3-lm]-β-carboline were obtained. Yield: 97%

M.p. 87°–91° C.
Mass (m/e): 310 (M+)
IR$\nu_{max}^{Nujol}$ (cm$^{-1}$): 1720, 1695, 1615, 765
NMR (δ, CDCl$_3$): 8.66–8.23 (m, 1H, aromatic); 7.64–7.00 (m, 3H, aromatic); 4.23–3.57 (m, 1H,

2.17 (s, 3H, —COCH$_3$); 3.50–1.33 (m, 14H)
Rf-value: 0.58 (Alumina, 1% methanol-chloroform)
Hydrochloride:
M.p. 285.5°–287° C. (decomp.) (colorless needles) (recrystallized from a mixture of isopropylalcohol and methanol)
IR$\nu_{max}^{Nujol}$ (cm$^{-1}$): 2320, 1720, 1700, 1625

EXAMPLE 60

10 ml of methyl acetate and 0.1 ml of acetic acid were added to 2.40 g of 1,2,3,3a,4,5,6,7-octahydro-7-oxoazepino[1,2,3-lm]-β-carboline, and the mixture was stirred at 50° C. (oil bath temperature) for 3 hours. After the reaction was completed, the reaction mixture was poured into ice-water. The aqueous mixture was alkalized with potassium carbonate, and then extracted with ethyl acetate. The extract was washed with water, dried and then condensed. The resultant oil (3 g) was recrystallized from isopropyl ether, whereby 2.67 g of 1,3,3a,4,5,6,7-octahydro-3-(2-methoxycarbonylethyl)-7-oxoazepino[1,2,3-lm]-β-carboline were obtained. Yield: 82%

M.p. 85.5°–87° C.
IR$\nu_{max}^{Nujol}$ (cm$^{-1}$): 1730, 1690, 1620, 770
Mass (m/e): 326 (M+)
NMR (δ, CDCl$_3$): 8.66–8.21 (m, 1H, aromatic); 7.66–7.07 (m, 3H, aromatic); 3.68 (s, 3H, —COOCH$_3$); 4.17–3.50 (m, 1H,

3.33–1.40 (m, 14H)
Hydrochloride:

M.p. 201.5°–203° C. (decomp.) (colorless needles) (recrystallized from a mixture of methanol and ethyl acetate)

IR$\nu_{max}^{Nujol}$ (cm$^{-1}$): 2450, 2400, 1740, 1690

EXAMPLE 61

(1) 15 ml of dimethylformamide, 1.06 g of 2-(tetrahydropyran-2-yl-oxy)ethyl chloride, 0.97 g of potassium carbonate and 0.1 g of potassium iodide were added to 1.30 g of 1,2,3,3a,4,5,6,7-octahydro-7-oxo-azepino[1,2,3-lm]-β-carboline, and the mixture was stirred at 80° C. for 4 hours. After the reaction was completed, the reaction mixture was poured into ice-water and the aqueous mixture was extracted with ethyl acetat. The extract was washed with water, dried and condensed. The oily residue thus obtained was purified by silica gel chromatography (Solvent: 1% methanol-chloroform), whereby 934 mg of 1,2,3,3a,4,5,6,7-octahydro-3-[2-(tetrahydropyran-2-yl-oxy)ethyl]-7-oxo-azepino[1,2,3-lm]-β-carboline were obtained as an oil. Yield: 47%

IR$\nu_{max}^{film}$ (cm$^{-1}$): 1695, 1620, 760
Mass (m/e): 368 (M+)
NMR (δ, CDCl$_3$): 8.67–8.30 (m, 1H, aromatic); 7.73–7.13 (m, 3H, aromatic); 4.63 (broad, 1H

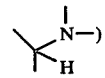

4.83–2.52 (m, 13H); 2.50–1.00 (m, 10H)
Rf-value: 0.67 (Silica gel, 6% methanol-chloroform)

(2) 40 ml of 50% aqueous ethanol and 3 ml of conc. hydrochloric acid were added to 900 mg of 1,2,3,3a,4,5,6,7-octahydro-3-[2-(tetrahydropyran-2-yl-oxy)ethyl]-7-oxo-azepino[1,2,3-lm]-β-carboline, and the mixture was stirred at room temperature for 24 hours. After the reaction was completed, the reaction mixture was evaporated under reduced pressure to remove solvent. Ethyl acetate was added to the residue thus obtained, and the mixture was alkalized with a dilute potassium carbonate solution under ice-cooling, and then extracted with ethyl acetate. The extract was washed with water, dried and condensed. The oily residue thus obtained was purified by silica gel chromatography (Solvent: 5% methanol-chloroform), whereby 600 mg of 1,2,3,3a,4,5,6,7-octahydro-3-(2-hydroxyethyl)-7-oxo-azepino[1,2,3-lm]-β-carboline were obtained as an oil. Yield: 77%

IR$\nu_{max}^{film}$ (cm$^{-1}$): 3430, 1690, 1620, 760
Mass (m/e): 284 (M+)
NMR (δ, CDCl$_3$): 8.67–8.27 (m, 1H, aromatic); 7.67–7.13 (m, 3H, aromatic); 4.27–3.43 (m, 3H); 3.67 (t, J=5.3 Hz, 2H, N—CH$_2$CH$_2$OH) 2.85 (t, J=5.3 Hz, 2H N—CH$_2$CH$_2$OH) 2.76 (s, 1H, —CH$_2$CH$_2$OH) 3.34–2.46 (m, 6H) 2.40–1.40 (m, 4H)

Rf-value: 0.31 (Silica gel, 5% methanol-chloroform)
Hydrochloride:
M.p. 226°–228° C. (decomp.) (needles) (recrystallized from methanol)
IR$\nu_{max}^{Nujol}$ (cm$^{-1}$): 3240, 2650, 2580, 1690, 1625, 755, 745

EXAMPLE 62

20 ml of tertiary amylalcohol and 40 ml of anhydrous tetrahydrofurane were added to 1.84 g of 1,2,3,3a,4,5,6,7-octahydro-3-acetylmethyl-7-oxo-azepino[1,2,3-lm]-β-carboline, and 1.14 g of sodium borohydride were added thereto. The mixture was stirred at room temperature for 4 hours. After the reaction was completed, the reaction mixture was acidified with acetic acid under ice-cooling, and then evaporated under reduced pressure to remove solvent. Ethyl acetate and a saturated sodium bicarbonate solution were added to the residue under ice-cooling, and the ethyl acetate layer was washed with water, dried and then condensed. The residue thus obtained was purified by silica gel chromatography (Solvent: 1.5% methanol-chloroform), whereby 1.30 g of 1,2,3,3a,4,5,6,7-octahydro-3-(2-hydroxy-n-propyl)-7-oxo-azepino-[1,2,3-lm]-β-carboline were obtained. Yield: 70%

M.p. 105°–107.5° C. (recrystallized from n-hexane)

IR$\nu_{max}^{Nujol}$ (cm$^{-1}$): 3420, 1690, 1615, 755

Mass (m/e): 298 (M+)

NMR (δ, CDCl$_3$): 8.73–8.30 (m, 1H, aromatic); 7.73–7.17 (m, 3H, aromatic); 4.33–3.50 (m, 2H); 3.50–1.50 (m, 13H); 1.15 (d, d, J=2.7 Hz, 6.0 Hz, 3H, NCH$_2$CH(OH)CH$_3$)

Hydrochloride:

M.p. 228°–230° C. (decomp.) (colorless needles) (recrystallized from a mixture of isopropylalcohol and methanol)

IR$\nu_{max}^{Nujol}$ (cm$^{-1}$): 3260, 2720–2570, 1695, 1625, 755, 745

EXAMPLE 63

(1) 40 ml of acetonitrile were added to 2.40 g of 1,2,3,3a,4,5,6,7-octahydro-7-oxo-azepino[1,2,3-lm]-β-carboline, and 1.03 g of anhydrous potassium carbonate, 100 mg of potassium iodide and 2.46 g of cyclohepten-3-yl bromide were added thereto. The mixture was stirred at 60° C. for 8 hours. After the reaction was completed, the reaction mixture was poured into ice-water, and the aqueous mixture was extracted with ethyl acetate. The extract was washed with a saturated sodium chloride solution, dried and then condensed. The residue thus obtained was purified by silica gel chromatography (Solvent: 1% methanol-chloroform), whereby 2.2 g of 1,2,3,3a,4,5,6,7-octahydro-3-(cycloheptan-3-yl)-7-oxo-azepino[1,2,3-lm]-β-carboline were obtained as a yellow oil. Yield: 63.9%

IR$\nu_{max}^{CHCl_3}$ (cm$^{-1}$): 1700

Mass (m/e): 344 (M+)

Rf-value: 0.83 (Silica gel, 5% methanol-chloroform)

Hydrochloride:

M.p. 215°–217° (decomp.) (colorless prisms) (recrystallized from ethanol)

IR$\nu_{max}^{Nujol}$ (cm$^{-1}$): 2220, 1698

Mass (m/e): 344 (M+)

NMR (δ, CDCl$_3$): 8.48 (m, 1H, aromatic); 7.37 (m, 3H, aromatic); 6.06 (m, 2H, allylic); 5.16–4.66 (m, 1H,

(2) 50 ml of ethanol and 250 mg of 10% palladium-carbon were added to 1.0 g of 1,2,3,3a,4,5,6,7-octahydro-3-(cyclohepten-3-yl)-7-oxo-azepino[1,2,3-lm]-β-carboline hydrochloride. The mixture was shaken at room temperature for 15 minutes in hydrogen atmosphere under atomspheric pressure. After hydrogen uptake was completed, insoluble materials were removed by filtration. The filtrate was condensed to dryness. The residue thus obtained was alkalized with a saturated sodium bicarbonate solution under cooling, and then extracted with chloroform. The extract was washed with water, dried and then condensed. The residue thus obtained was purified by silica gel chromatography (Solvent: 5% methanol-chloroform), whereby 810 mg of 1,2,3,3a,4,5,6,7-octahydro-3-cycloheptyl-7-oxo-azepino[1,2,3-lm]-β-carboline were obtained.

IR$\nu_{max}^{CHCl_3}$ (cm$^{-1}$): 1695

Mass (m/e): 336 (M+)

Hydrochloride:

M.p. 238°–240° C. (decomp.) (colorless scales) recrystallized from a mixture of ethanol and isopropylalcohol)

IR$\nu_{max}^{Nujol}$ (cm$^{-1}$): 2400, 1700

NMR (δ, CDCl$_3$): 8.50–8.33 (m, 1H, aromatic); 7.60–7.15 (m, 3H, aromatic); 5.16–4.66 (m, 1H

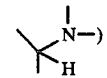

What we claim is:

1. An azepino[1,2,3-lm]-β-carboline compound of the formula:

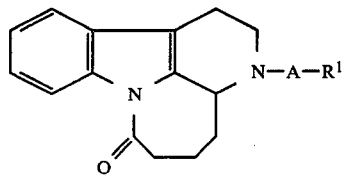

wherein R$^1$ is hydrogen, cycloalkyl of 3 to 7 carbon atoms, phenyl, hydroxy, alkoxycarbonyl of 2 or 3 carbon atoms or alkanoyl of 2 or 3 carbon atoms, and A is single bond or straight or branched alkylene of one to 5 carbon atoms, or a pharmaceutically acceptable acid addition salt thereof.

2. The compound of claim 1 wherein R$^1$ is hydrogen, cycloalkyl of 6 or 7 carbon atoms, phenyl hydroxy or acetyl.

3. The compound of claims 1 or 2 wherein R$^1$ is cycloalkyl of 6 or 7 carbon atoms or phenyl, and A is single bond or methylene.

4. The compound of claim 3 which is 1,2,3,3a,4,5,6,7-octahydro-3-cycloheptyl-7-oxo-azepino[1,2,3-lm]-β-carboline or a pharmaceutically acceptable acid addition salt thereof.

5. The compound of claim 3 which is 1,2,3,3a,4,5,6,7-octahydro-3-cyclohexylmethyl-7-oxo-azepino[1,2,3-lm]-β-carboline or a pharmaceutically acceptable acid addition salt thereof.

6. The compound of claim 3 which is 1,2,3,3a,4,5,6,7-octahydro-3-benzyl-7-oxo-azepino[1,2,3-lm]-β-carboline or a pharmaceutically acceptable acid addition salt thereof.

7. An anti-anoxic composition consisting essentially of a compound of claim 1 and a pharmaceutically acceptable carrier, in an amount sufficient to provide a therapeutically effective amount of said compound when administered to warm blooded animals.

* * * * *